(12) United States Patent
Bruner et al.

(10) Patent No.: US 10,806,748 B2
(45) Date of Patent: Oct. 20, 2020

(54) COMPOSITIONS AND METHODS RELATED TO CHARACTERIZING PROVIRAL RESERVOIRS

(71) Applicant: The Johns Hopkins University, Baltimore, MD (US)

(72) Inventors: Katherine Bruner, Nottingham, MD (US); Robert Siliciano, Baltimore, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 161 days.

(21) Appl. No.: 15/568,893

(22) PCT Filed: Apr. 22, 2016

(86) PCT No.: PCT/US2016/028822
§ 371 (c)(1),
(2) Date: Oct. 24, 2017

(87) PCT Pub. No.: WO2016/172465
PCT Pub. Date: Oct. 27, 2016

(65) Prior Publication Data
US 2018/0214473 A1  Aug. 2, 2018

Related U.S. Application Data

(60) Provisional application No. 62/152,436, filed on Apr. 24, 2015.

(51) Int. Cl.
*C12Q 1/68* (2018.01)
*A61K 31/711* (2006.01)
*C12Q 1/6806* (2018.01)
*C12Q 1/70* (2006.01)
*A61P 31/18* (2006.01)
(Continued)

(52) U.S. Cl.
CPC ............ *A61K 31/711* (2013.01); *A61P 31/18* (2018.01); *C12Q 1/68* (2013.01); *C12Q 1/6806* (2013.01); *C12Q 1/703* (2013.01); *G01N 33/5308* (2013.01); *G01N 33/56983* (2013.01)

(58) Field of Classification Search
None
See application file for complete search history.

(56) References Cited

U.S. PATENT DOCUMENTS 6,448,014 B2   9/2002  Cloyd et al.
8,535,889 B2   9/2013  Larson et al.
(Continued)

FOREIGN PATENT DOCUMENTS

EP        0591914 A2 *  4/1994  ....... G01N 33/56988
WO    WO-0220571 A2 *  3/2002
WO    WO-2013/134458 A1  9/2013

OTHER PUBLICATIONS

Haesevelde et al, J. Virol. 68(3): 1586-1596, 1994.*
(Continued)

*Primary Examiner* — Aaron A Priest
(74) *Attorney, Agent, or Firm* — Ballard Spahr LLP

(57) ABSTRACT

In some aspects, the invention relates to methods for determining the proportion of intact, hypermutated, deleted, and/or defective proviruses in a sample of nucleic acids, e.g., a sample obtained from a subject. The subject may be a human subject. The virus may be HIV.

25 Claims, 11 Drawing Sheets
Specification includes a Sequence Listing.

(51) Int. Cl.
*G01N 33/53* (2006.01)
*G01N 33/569* (2006.01)

(56) References Cited

U.S. PATENT DOCUMENTS

| | | | |
|---|---|---|---|
| 8,748,088 B2 | 6/2014 | Stevenson | |
| 2001/0034020 A1 | 10/2001 | Zimmermann et al. | |
| 2006/0172325 A1* | 8/2006 | Brownstein | C12Q 2537/143 435/6.16 |
| 2008/0267993 A1* | 10/2008 | Haigwood | C07K 14/005 424/202.1 |
| 2013/0184335 A1 | 7/2013 | Miura | |
| 2013/0266931 A1* | 10/2013 | Jolly | C12Q 1/702 435/5 |

OTHER PUBLICATIONS

Nolan et al. (Quantification of mRNA using real-time RT-PCR, Nature Protocols, vol. 1, No. 3, Nov. 9, 2006).*
NCBI Accession No. KF526333, attached, Sep. 16, 2013.*
Janini, M. et al: "Human Immunodeficiency Virus Type 1 DNA Sequences Genetically Damaged by Hypermutation are Often Abundant in Patient Peripheral Blood Mononuclear Cells and may be Generated during Near-Simultaneous Infection and Activation of CD4+ T Cells", Journal of Virology., vol. 75, No. 17, (2001), pp. 7973-7986.
European Search Report dated Sep. 13, 2018 by the European Patent Office for EP Application No. 16783931.5, which was filed on Apr. 22, 2016 and published as EP 3286335 on Feb. 28, 2018 (Applicant—The John Hopkins University) (9 pages).
Anderson et al., "Clonal sequences recovered from plasma from patients with residual HIV-1 viremia and on intensified antiretroviral therapy are identical to replicating viral RNAs recovered from circulating resting CD4+ T cells," J Virol, 85:5220-5223 (2011).
Archin et al., "Administration of vorinostat disrupts HIV-1 latency in patients on antiretroviral therapy," Nature 487:482-485 (2012).
Archin et al., "Emerging strategies to deplete the HIV reservoir," Curr Opin Infect Dis, 27:29-35 (2014).
Archin et al., "Expression of latent HIV induced by the potent HDAC inhibitor suberoylanilide hydroxamic acid," AIDS Res Hum Retroviruses, 25:207-212 (2009).
Archin et al., "HIV-1 Expression Within Resting CD4+ T Cells After Multiple Doses of Vorinostat," J Infect Dis, 210:728-735 (2014).
Arnedo-Valero et al., "Risk of selecting de novo dvug-resistance mutations during structured treatment interruptions in patients with chronic HIV infection," Clin Infect Dis, 41:883-890 (2005).
Bagasra et al., "Detection of human immunodeficiency virus type 1 provirus in mononuclear cells by in situ polymerase chain reaction," N Engl J Med, 326(21):1385-1391 (1992).
Bailey et al., "Residual human immunodeficiency virus type 1 viremia in some patients on antiretroviral therapy is dominated by a small numbe of invariant clones rarely found in circulating CD4+ T cells," J Virol, 80:6441-6457 (2006).
Besson et al., "Short-course raltegravir intensification does not increase 2 long terminal repeat episomal HIV-1 DNA in patients on effective antiretroviral therapy," Clin Infect Dis, 54:451-453 (2012).
Blankson et al., "Biphasic decay of latently infected CD4+ T cells in acute human immunodeficiency virus type 1 infection," J Infect Dis, 182:1636-1642 (2000).
Blazkova et al., "Effect of histone deacetylase inhibitors on HIV production in latently infected, resting CD4(+) T cells from infected individuals receiving effective antiretroviral therapy," J Infect Dis, 206:765-769 (2012).
Brenchley et al., "T-cell subsets that harbor human immunodeficiency virus (HIV) in vivo: implications for HIV pathogenesis," J Virol, 78:1160-1168 (2004).

Bullen et al., "New ex vivo approaches distinguish effective and ineffective single agents for reversing HIV-1 latency in vivo," Nat Med, 20:425-429 (2014).
Butler et al., "A quantitative assay for HIV DNA integration in vivo," Nat Med, 7:631-634 (2001).
Buzon et al., "HIV-1 persistence in CD4+ T cells with stem cell-like properties," Nat Med, 20:139-142 (2014).
Buzon et al., "HIV-1 replication and immune dynamics are affected by raltegravir intensification of HAART-suppressed subjects," Nat Med, 16:46065 (2010).
Chomont et al., "HIV reservoir size and persistence are driven by T cell survival and homeostatic proliferation," Nat Med, 15:893-900 (2009).
Chun et al., "In vivo fate of HIV-1-infected T cells: quantitative analysis of the transition to stable latency," Nat Med, 1:1284-1290 (1995).
Chun et al., "Persistence of HIV in Gut-Associated Lymphoid Tissue despite Long-Term Antiretroviral Therapy," J Infect Dis, 197:714-720 (2008).
Chun et al., "Presence of an inducible HIV-1 latent reservoir during highly active antiretroviral therapy," Proc Natl Acad Sci USA, 94:13193-13197 (1997).
Chun et al., "Quantification of latent tissue reservoirs and total body viral load in HIV-1 infection," Nature, 387:183-188 (1997).
Chun et al., "Relationship between residual plasma viremia and the size of HIV proviral DNA reservoirs in infected individuals receiving effective antiretroviral therapy," J Infect Dis, 204:135-138 (2011).
Cillo et al., "Improved Single-Copy Assays for Quantification of Persistent HIV-1 Viremia in Patients on Suppressive Antiretroviral Therapy," J Clin Microbiol, 52:3944-3951 (2014).
Cillo et al., "Plasma viremia and cellular HIV-1 DNA persist despite autologous hematopoietic stem cell transplantation for HIV-related lymphoma," J Acquir Immune Defic Syndr 63:438-441 (2013).
Cillo et al., "Quantification of HIV-1 latency reversal in resting CD4+ T cells from patients on suppressive antiretroviral therapy," Proc Natl Acad Sci USA, 111:7078-7083 (2014).
Dahl et al., "Single-copy assay quantification of HIV-1 RNA in paired cerebrospinal fluid and plasma samples from elite controllers," AIDS, 27:1145-1149 (2013).
Davey et al., "HIV-1 and T cell dynamics after interruption of highly active antiretroviral therapy (HAART) in patients with a history of sustained viral suppression," Proc Natl Acad Sci USA, 96:15109-15114 (1999).
De Lima-Stein et al., "In Vivo HIV-1 Hypermutation and Viral Loads Among Antiretroviral-Naive Brazilian Patients," AIDS Res Hum Retroviruses, 30(9):867-880 (2014).
De Spiegelaere et al., "Quantification of integrated HIV DNA by repetitive-sampling Alu-HIV PCR on the basis of poisson statistics," Clin Chem, 60(6):886-895 (2014).
Deeks et al., "Towards an HIV cure: a global scientific strategy," Nat Rev Immunol, 12:607-614 (2012).
Deeks, "HIV: Shock and kill," Nature, 487:439-440 (2012).
Dinoso et al., "Treatment intensification does not reduce residual HIV-1 viremia in patients on highly active antiretroviral therapy," Proc Natl Acad Sci USA 106:9403-9408 (2009).
Durand et al., "Developing strategies for HIV-1 eradication," Trends Immunol, 33:554-562 (2012).
Durand et al., "HIV-1 DNA is detected in bone marrow populations containing CD4+ T cells but is not found in purified CD34+ hematopoietic progenitor cells in most patients on antiretroviral therapy," J Infect Dis, 205:1014-1018 (2012).
Eriksson et al., "Comparative analysis of measures of viral reservoirs in; HIV-1 eradication studies," PLoS Pathog, 9:e1003174 (2013).
Farnet et al., "Circularization of human immunodeficiency virus type 1 DNA in vitro," J Virol, 65(12):6942-6952 (1991).
Finzi et al., "Identification of a reservoir for HIV-1 in patients on highly active antiretroviral therapy," Science, 278:1295-1300 (1997).
Finzi et al., "Latent infection of CD4+ T cells provides a mechanism for lifelong persistence of HIV-1, even in patients on effective combination therapy," Nat Med, 5:512-517 (1999).

(56) References Cited

OTHER PUBLICATIONS

Gandhi et al., "No effect of raltegravir intensification on viral replication markers in the blood of HIV-1-infected patients receiving antiretroviral therapy," J Acquir Immune Defic Syndr, 59:229-235 (2012).
Han et al., "Resting CD4+ T cells from human immunodeficiency virus type 1 (HIV-1)-infected individuals carry integrated HIV-1 genomes within actively transcribed host genes," J Virol, 78:6122-6133 (2004).
Hatano et al., "Comparison of HIV DNA and RNA in gut-associated lymphoid tissue of HIV-infected controllers and noncontrollers," AIDS, 27:2255-2260 (2013).
Hatano et al., "Evidence for persistent low-level viremia in individuals who control human immunodeficiency virus in the absence of antiretroviral therapy," J Virol, 83:329-335 (2009).
Henrich et al., "Antiretroviral-Free HIV-1 Remission and Viral Rebound After Allogeneic Stem Cell Transplantation: Report of 2 Cases," Ann Intern Med, 161:319-327 (2014).
Henrich et al., "Long-term reduction in peripheral blood HIV type 1 reservoirs following reduced-intensity conditioning allogeneic stem cell transplantation," J Infect Dis, 207:1694-1702 (2013).
Henrich et al., "Low-level detection and quantitation of cellular HIV-1 DNA and 2-LTR circles using droplet digital PCR," J Virol Methods, 186:68-72 (2012).
Hermankova et al., "Analysis of human immunodeficiency virus type 1 gene expression in latently infected resting CD4+ T lymphocytes in vivo," J Virol, 77:7383-7392 (2003).
Hermankova et al., "HIV-1 drug resistance profiles in children and adults with viral load of <50 copies/ml receiving combination therapy," JAMA 286:196-207 (2001).
Hill et al., "Predicting the outcomes of treatment to eradicate the latent reservoir for HIV-1," Proc Natl Acad Sci USA, 111:13475-1380 (2014).
Ho et al., "Replication-competent noninduced proviruses in the latent reservoir increase barrier to HIV-1 cure," Cell, 155:540-551 (2013).
Hütter et al., "Long-term control of HIV by CCR5 Delta32/Delta32 stem-cell transplantation," N Engl J Med, 360:692-698 (2009).
International Search Report and Written Opinion for International Application No. PCT/US2016/028822 dated Aug. 11, 2016.
Jones et al., "Low copy target detection by Droplet Digital PCR through application of a novel open access bioinformatic pipeline, 'definetherain," J Virol Methods, 202:46-53 (2014).
Kieffer et al., "G→ A hypermutation in protease and reverse transcriptase regions of human immunodeficiency virus type 1 residing in resting CD4+ T cells in vivo," J Virol, 79:1975-1980 (2005).
Kieffer et al., "Genotypic analysis of HIV-1 drug resistance at the limit of detection: virus production without evolution in treated adults with undetectable HIV loads," J Infect Dis, 189:1452-1465 (2004).
Laird et al., "Rapid Quantification of the Latent Reservoir for HIV-1 Using a Viral Outgrowth Assay," PLoS Pathog, 9:e1003398 (2013).
Luebbert et al., "Virological failure and drug resistance in patients on antiretroviral therapy after treatment interruption in Lilongwe, Malawi," Clin Infect Dis, 55:441-448 (2012).
Margolis et al., "How might we cure HIV?," Curr Infect Dis Rep, 16:392-395 (2014).
Markowitz et al., "A Randomized Open-Label Study of Three-versus Five-Drug Combination Antiretroviral Therapy in Newly HIV-1 Infected Individuals," J Acquir Immune Defic Syndr, 66:140-147 (2014).
McBride et al., "The majority of HIV type 1 DNA in circulating CD4+ T lymphocytes is present in non-gut-homing resting memory CD4+ T cells," AIDS Res Hum Retroviruses, 29:1330-1339 (2013).
Murray et al., "Integrated HIV DNA accumulates prior to treatment while episomal HIV DNA records ongoing transmission afterwards," AIDS, 26:543-550 (2012).

O'Doherty et al., "A sensitive, quantitative assay for human immunodeficiency virus type 1 integration," J Virol, 76:10942-10950 (2002).
Pace et al., "A cure for HIV: is it in sight?" Expert Rev Anti Infect Ther, 12:783-791 (2014).
Pace et al., "HIV 2—Long Terminal Repeat Circular DNA is Stable in Primary CD4+ T Cells," Virology, 441(1):18-21 (2013).
Palmer et al., "New real-time reverse transcriptase-initiated PCR assay with single-copy sensitivity for human immunodeficiency virus type 1 RNA in plasma," J Clin Microbiol, 41:4531-4536 (2003).
Palmer, "Advances in detection and monitoring of plasma viremia in HIV infected individuals receiving antiretroviral therapy," Curr Opin HIV AIDS, 8:87-92 (2013).
Perelson et al., "Decay characteristics of HIV-1-infected compartments during combination therapy," Nature 387, 188-191 (1997).
Persaud et al., "Absence of detectable HIV-1 viremia after treatment cessation in an infant," N Engl J Med, 369:1828-1835 (2013).
Pierson et al., "Intrinsic stability of episomal circles formed during human immunodeficiency virus type 1 replication," J Virol, 76:4138-4144 (2002).
Pierson et al., "Molecular characterization of preintegration latency in human immunodeficiency virus type 1 infection," J Virol, 76:8518-8531 (2002).
Procopio et al., "A Novel Assay That Precisely Measures the Size of the Latent HIV Reservoir Reveals That Art-Naive Individuals Harbour a Large Pool of Latently Infected Cd4+ T Cells," International AIDS Society, Towards and HIV Cure Symposium, Abstract 11147 (2014).
Puertas et al., "Intensification of a raltegravir-based regimen with maraviroc in early HIV-1 infection," AIDS, 28:325-334 (2014).
Rasmussen et al., "Panobinostat, a histone deacetylase inhibitor, for latent- virus reactivation in HIV-infected patients on suppressive antiretroviral therapy: a phase 1/2, single group, clinical trial," The Lancet HIV, 1:e13-e21 (2014).
Rose et al., "Detecting hypermutations in viral sequences with an emphasis on G→ A hypermutation," Bioinformatics, 16:400-401 (2000).
Routy et al., "Assessing risk of a short-term antiretroviral therapy discontinuation as a read-out of viral control in immune-based therapy," J Med Virol, 84, 885-889 (2012).
Ruelas et al., "An integrated overview of HIV-1 latency," Cell 155:519-529 (2013).
Sahu et al., "Recovery of replication-competent residual HIV-1 from plasma of a patient receiving prolonged, suppressive highly active antiretroviral therapy," J Virol, 84:8348-8352 (2010).
Sanchez et al., "Accumulation of defective viral genomes in peripheral blood mononuclear cells of human immunodeficiency virus type 1-infected; individuals," J Virol, 71, 2233-2240 (1997).
Shan et al., "Stimulation of HIV-1-specific cytolytic T lymphocytes facilitates elimination of latent viral reservoir after virus reactivation," Immunity, 36:491-501 (2012).
Shirakawa et al., "Reactivation of latent HIV by histone deacetylase inhibitors," Trends Microbiol, 21:277-285 (2013).
Siliciano et al., "Long-term follow-up studies confirm the stability of the latent reservoir for HIV-1 in resting CD4+ T cells," Nat Med, 9:727-728 (2003).
Siliciano et al., "Rekindled HIV infection," Science, 345:1005-1006 (2014).
Silverberg et al., "Risk of cancers during interrupted antiretroviral therapy in the SMART study," AIDS, 21:1957-1963 (2007).
Simon-Loriere et al., Why do RNA viruses recombine? Nat Rev Microbiol, 9:617-626 (2011).
Stevenson et al., "Integration is not necessary for expression of human immunodeficiency virus type 1 protein products," J Virol, 64:2421-2425 (1990).
Stopak et al., "HIV-1 Vif blocks the antiviral activity of APOBEC3G by impairing both its translation and intracellular stability," Mol Cell, 12:591-601 (2003).
Strain et al., "Highly precise measurement of HIV DNA by droplet digital PCR," PLoS One, 8:e55943 (2013).
Tebas et al., "Gene editing of CCR5 in autologous CD4 T cells of persons infected with HIV," N Engl J Med, 370:901-910 (2014).

(56) References Cited

OTHER PUBLICATIONS

The Strategies for Management of Antiretroviral Therapy (SMART) Study Group, "CD4+ count-guided interruption of antiretroviral treatment," N Engl J Med, 355:2283-2296 (2006).

Tobin et al., "Evidence that low-level viremias during effective highly active antiretroviral therapy result from two processes: expression of archival virus and replication of virus," J Virol, 79:9625-9634 (2005).

Vandegraaff et al., "Kinetics of human immunodeficiency virus type 1 (HIV) DNA integration in acutely infected cells as determined using a novel assay for detection of integrated HIV DNA," J Virol, 75(22):11253-11260 (2001).

Wei et al., "Histone deacetylase inhibitor romidepsin induces HIV expression in CD4 T cells from patients on suppressive antiretroviral therapy at concentrations achieved by clinical dosing," PLoS Pathog, 10:e1004071 (2014).

Wong et al., "Recovery of replication-competent HIV despite prolonged suppression of plasma viremia," Science, 278:1291-1295 (1997).

Wren et al., "Obstacles to ideal anti-HIV antibody-dependent cellular cytotoxicity responses," Vaccine 31:5506-5517 (2013).

Ylisastigui et al., "Coaxing HIV-1 from resting CD4 T cells: histone deacetylase inhibition allows latent viral expression," AIDS, 18:1101-1108 (2014).

Yoder et al., "PCR-based detection is unable to consistently distinguish HIV 1 LTR circles," J Virol Methods, 138:201-206 (2006).

Yu et al., "Single-strand specificity of APOBEC3G accounts for minusstrand; deamination of the HIV genome," Nat Struct Mol Biol, 11:435-442 (2004).

Yuki et al., "Challenges in detecting HIV persistence during potentially curative interventions: a study of the Berlin patient," PLoS Pathog, 9:e1003347 (2013).

Yuki et al., "Differences in HIV burden and immune activation within the gut of HIV-positive patients receiving suppressive antiretroviral therapy," J Infect Dis, 202:1553-1561 (2010).

Zack et al., "HIV-1 entry into quiescent primary lymphocytes: molecular analysis reveals a labile, latent viral structure," Cell, 61:213-222 (1990).

Zhu et al., "Rapid turnover of 2-LTR HIV-1 DNA during early stage of highly active antiretroviral therapy," PLoS One, 6:e21081 (2011).

\* cited by examiner

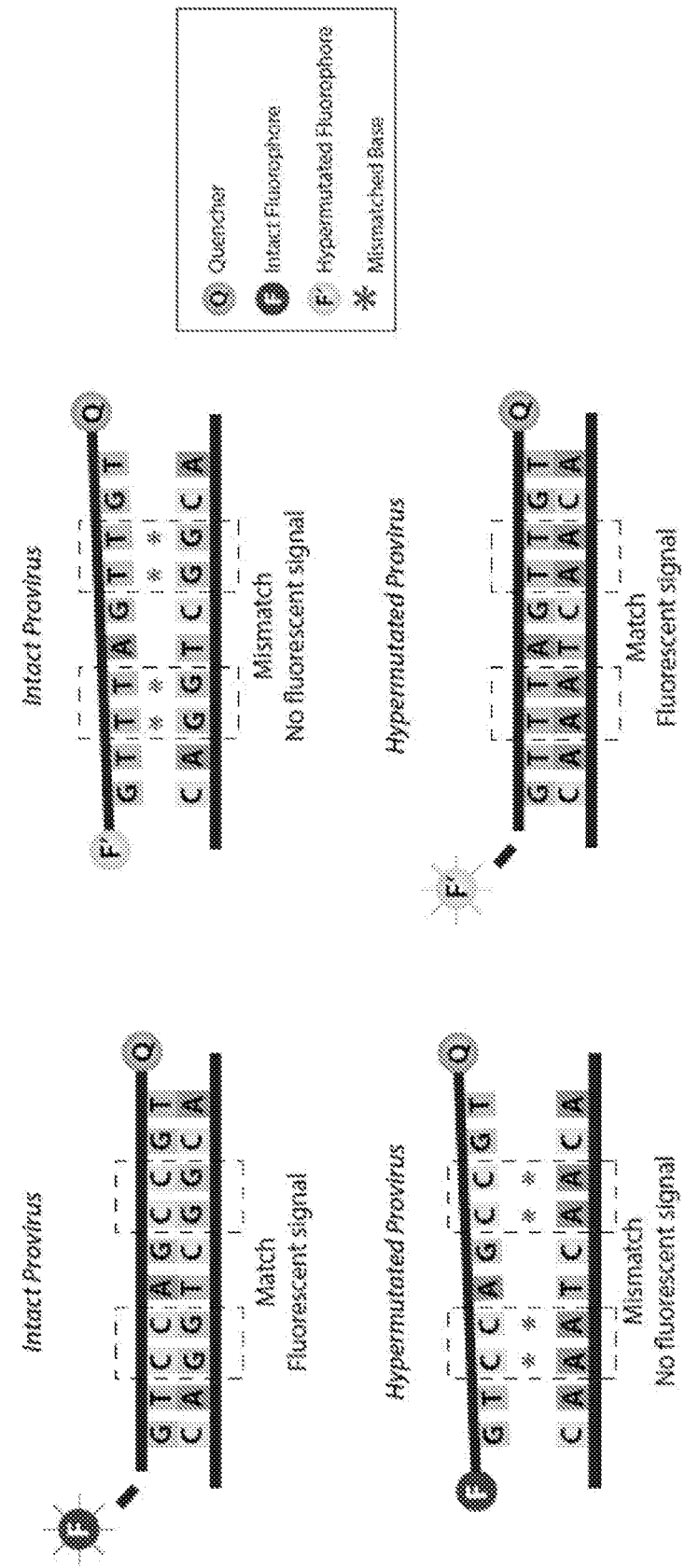

Figure 7
Single round of infection
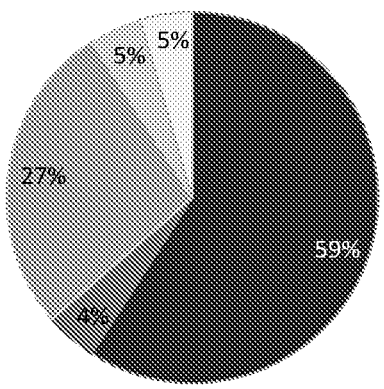
N = 22 sequences
Viremic patients
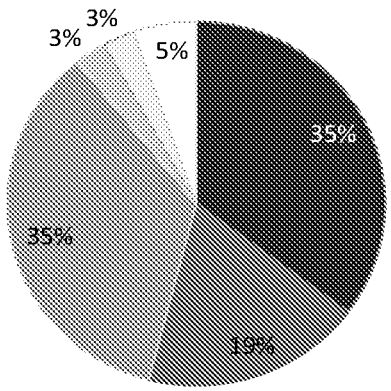
N = 2 patients, 37 sequences
Acutely treated patients
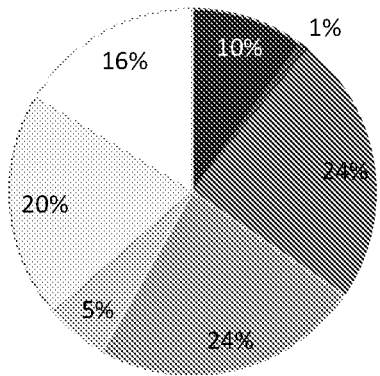
N = 7 patients, 110 sequences
Chronically treated patients
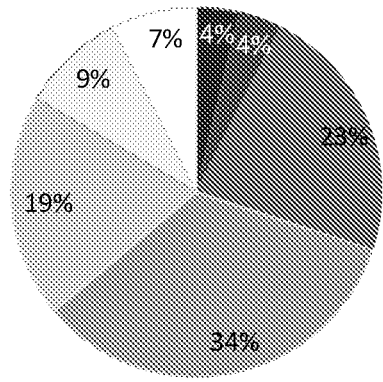
N = 9 patients, 133 sequences
Key:
- Intact
- Hypermutated
- Hypermutated and deleted
- Packaging signal deletion
- Deletion at 5' end of the genome
- Deletion at 3' end of the genome
- Very large internal deletion

SEQUENCE LISTING

```
<160> NUMBER OF SEQ ID NOS: 17

<210> SEQ ID NO 1
<211> LENGTH: 18
<212> TYPE: DNA
<213> ORGANISM: Artificial Sequence
<220> FEATURE:
<223> OTHER INFORMATION: Synthetic construct

<400> SEQUENCE: 1
tctctcgacg caggactc                                                   18

<210> SEQ ID NO 2
<211> LENGTH: 20
<212> TYPE: DNA
<213> ORGANISM: Artificial Sequence
<220> FEATURE:
<223> OTHER INFORMATION: Synthetic construct

<400> SEQUENCE: 2
tctagcctcc gctagtcaaa                                                 20

<210> SEQ ID NO 3
<211> LENGTH: 22
<212> TYPE: DNA
<213> ORGANISM: Artificial Sequence
<220> FEATURE:
<223> OTHER INFORMATION: Synthetic construct

<400> SEQUENCE: 3
tttggcgtac tcaccagtcg cc                                              22

<210> SEQ ID NO 4
<211> LENGTH: 24
<212> TYPE: DNA
<213> ORGANISM: Artificial Sequence
<220> FEATURE:
<223> OTHER INFORMATION: Synthetic construct

<400> SEQUENCE: 4
agtggtgcag agagaaaaaa gagc                                            24

<210> SEQ ID NO 5
<211> LENGTH: 20
<212> TYPE: DNA
<213> ORGANISM: Artificial Sequence
<220> FEATURE:
<223> OTHER INFORMATION: Synthetic construct

<400> SEQUENCE: 5
gtctggcctg taccgtcagc                                                 20
```

```
<210> SEQ ID NO 6
<211> LENGTH: 20
<212> TYPE: DNA
<213> ORGANISM: Artificial Sequence
<220> FEATURE:
<223> OTHER INFORMATION: Synthetic construct

<400> SEQUENCE: 6
ttccttaagt tcttaggagc                                              20

<210> SEQ ID NO 7
<211> LENGTH: 16
<212> TYPE: DNA
<213> ORGANISM: Artificial Sequence
<220> FEATURE:
<223> OTHER INFORMATION: Synthetic construct

<400> SEQUENCE: 7
ccttgggttc ttggga                                                  16

<210> SEQ ID NO 8
<211> LENGTH: 25
<212> TYPE: DNA
<213> ORGANISM: Artificial Sequence
<220> FEATURE:
<223> OTHER INFORMATION: Synthetic construct

<400> SEQUENCE: 8
catgttttca gcattatcag aagga                                        25

<210> SEQ ID NO 9
<211> LENGTH: 19
<212> TYPE: DNA
<213> ORGANISM: Artificial Sequence
<220> FEATURE:
<223> OTHER INFORMATION: Synthetic construct

<400> SEQUENCE: 9
tgcttgatgt cccccact                                                19

<210> SEQ ID NO 10
<211> LENGTH: 30
<212> TYPE: DNA
<213> ORGANISM: Artificial Sequence
<220> FEATURE:
<223> OTHER INFORMATION: Synthetic construct

<400> SEQUENCE: 10
ccaccccaca agatttaaac accatgctaa                                   30

<210> SEQ ID NO 11
<211> LENGTH: 27
<212> TYPE: DNA
<213> ORGANISM: Artificial Sequence
<220> FEATURE:
<223> OTHER INFORMATION: Synthetic construct

<400> SEQUENCE: 11
gcactttaaa ttttcccatt agtccta                                      27

<210> SEQ ID NO 12
<211> LENGTH: 29
<212> TYPE: DNA
<213> ORGANISM: Artificial Sequence
<220> FEATURE:
<223> OTHER INFORMATION: Synthetic construct
```

```
<400> SEQUENCE: 12
caaatttcta ctaatgcttt tattttttc                                              29

<210> SEQ ID NO 13
<211> LENGTH: 19
<212> TYPE: DNA
<213> ORGANISM: Artificial Sequence
<220> FEATURE:
<223> OTHER INFORMATION: Synthetic construct

<400> SEQUENCE: 13
aagccaggaa tggatggcc                                                         19

<210> SEQ ID NO 14
<211> LENGTH: 10
<212> TYPE: DNA
<213> ORGANISM: Artificial Sequence
<220> FEATURE:
<223> OTHER INFORMATION: Synthetic construct

<400> SEQUENCE: 14
gtccagccgt                                                                   10

<210> SEQ ID NO 15
<211> LENGTH: 10
<212> TYPE: DNA
<213> ORGANISM: Artificial Sequence
<220> FEATURE:
<223> OTHER INFORMATION: Synthetic construct

<400> SEQUENCE: 15
acggctggac                                                                   10

<210> SEQ ID NO 16
<211> LENGTH: 10
<212> TYPE: DNA
<213> ORGANISM: Artificial Sequence
<220> FEATURE:
<223> OTHER INFORMATION: Synthetic construct

<400> SEQUENCE: 16
acaactaaac                                                                   10

<210> SEQ ID NO 17
<211> LENGTH: 10
<212> TYPE: DNA
<213> ORGANISM: Artificial Sequence
<220> FEATURE:
<223> OTHER INFORMATION: Synthetic construct

<400> SEQUENCE: 17
gtttagttgt                                                                   10
```

COMPOSITIONS AND METHODS RELATED TO CHARACTERIZING PROVIRAL RESERVOIRS

PRIORITY

This application is a 371 National Stage Application of PCT/US16/028822, filed Apr. 22, 2016, which claims priority to U.S. Provisional Patent Application No. 62/152,436, filed on Apr. 24, 2015. The entire contents of these applications are hereby incorporated by reference in their entirety.

GOVERNMENT INTEREST

This invention was made with Government support under National Institutes of Health Grants R21AI113147, AI096113, 1U19AI096109, and 43222. The Government has certain rights in the invention.

INCORPORATION OF THE SEQUENCE LISTING

The present application contains a sequence listing submitted herewith via EFS-Web, containing the file name 36406_0014U2_SL which is 4,096 bytes in size, created on Feb. 11, 2020, and is herein incorporated by reference in its entirety pursuant to 37 C.F.R. § 1.52(e)(5).

BACKGROUND

Although combination antiretroviral therapy suppresses HIV-1 replication to clinically undetectable levels, the virus persists in a quiescent state in a subset of lymphocytes. This latent reservoir (LR) of virus found in resting memory $CD4^+$ T cells is the major barrier to a cure. HIV-1 preferentially infects activated $CD4^+$ T cells. However, in rare instances, a fully or partially activated $CD4^+$ T cell that has been infected with HIV-1 can return to a resting memory state. This transition from activated to resting memory cell is part of the normal physiology of $CD4^+$ T cells that have encountered their cognate antigens, and the transition is essential to the establishment of immunological memory. However, because resting memory $CD4^+$ T cells are largely non-permissive for viral gene expression, the infecting HIV-1 genome persists in a DNA form as an integrated provirus that is not actively transcribed. For this reason, latently infected cells are not targeted by the immune system or ART. Furthermore, because resting memory $CD4^+$ T cells are long-lived, the LR has an extremely long half-life of approximately 44 months. When ART is interrupted in HIV-1 infected patients, HIV-1 re-emerges from the LR and uncontrolled viral replication begins anew. The long half-life of the LR and its ability to re-emerge after interruption of ART necessitate continuous and lifelong treatment.

The latent reservoir (LR) was first identified and characterized in the mid-1990s using a viral outgrowth assay (VOA) for measuring the frequency of resting $CD4^+$ T cells that carry replication-competent proviruses in a latent state. The VOA involves maximal activation of the resting $CD4^+$ T cells in limiting dilution, which reactivates viral gene expression in latently infected cells and induces the release of infectious HIV-1 virions. The released virus is cultured and expanded with healthy donor lymphoblasts for 2-3 weeks and an ELISA against the HIV-1 p24 protein is used to quantify viral outgrowth. The frequency of latent infection can then be determined based on the pattern of viral outgrowth in the assay wells. Until recently, this assay was thought to be the definitive measurement of the LR. However, recent studies have shown that the VOA underestimates the true size of the LR because viral outgrowth is not observed in all VOA assay wells that contain cells with intact proviruses. When wells negative for viral outgrowth were stimulated a second time with PHA, outgrowth of replication-competent virus were observed. Additional outgrowth has also been observed following three and four rounds of cellular activation. These findings indicate that the LR is larger than previously thought and redefine the latent reservoir to include these genetically intact proviruses missed by the original VOA. Currently, the field has no way to measure this population of intact proviruses, which must be eliminated to achieve an HIV-1 cure.

Due to the labor-intensive nature of the VOA, there has been great interest in developing alternative assays. PCR-based assays that measure total HIV-1 proviral DNA have been advanced as simpler measures of the LR. Current PCR-based methods use only a single set of primers and probes to measure the HIV-1 LR. In doing so, they grossly overestimate the size of the LR and detect primarily defective proviruses that are intact in the primer binding region but defective elsewhere in the genome. However, these defective proviruses do not need to be eliminated to achieve a cure and may not be affected by eradication therapy. Although both culture- and PCR-based methods are commonly used, there is little correlation between the two types of assays. Based on the VOA, approximately 1 per $10^6$ resting $CD4^+$ T cells contain replication-competent virus, but PCR-based assays show that on average 300 per $10^6$ resting $CD4^+$ T cells contain HIV-1 proviral DNA. These discrepancies are attributed to the differences in what types of proviruses each assay specifically measures and indicate that neither class of assay accurately quantifies the LR. The actual size of the latent reservoir is thought to be approximately an order of magnitude larger than that measured by the VOA.

RNA measurements of proviruses are also quite common. In these assays, patient resting $CD4^+$ T cells are plated and maximally activated at limiting dilution such that there is less than one virus-producing cell per well. Following maximal T cell activation, the frequency of cells producing viral RNA is directly measured by a quantitative PCR (qPCR) specific for HIV mRNA in the cell or mRNA in the culture supernatant (presumably reflecting virion release). However, these assays also only involve a single round of T cell activation, and thus do not detect intact proviruses that are not induced after a single round of activation. Additionally, some defective proviruses may be able to produce HIV-1 RNA and even release non-infectious virions. These defective proviruses could be detected by these assays. Thus, this class of assays may be confounded by both false negative and false positive results and do not accurately measure the size of the LR. Accordingly, a reliable and sensitive assay that can accurately measure only intact proviruses is needed.

BRIEF DESCRIPTION

In some aspects, the invention relates to methods for determining the proportion of intact, hypermutated, deleted, and/or defective proviruses in a sample of nucleic acids, e.g., a sample obtained from a subject. The subject may be a human subject. The virus may be HIV.

DESCRIPTION OF THE FIGURES

FIG. 4. Series of probes allows for identification and distinction of intact and hypermutated proviruses. Two probes are designed to hybridize to the same region of DNA that is commonly hypermutated in patient sequences. The "intact" probe (designated F, a native viral sequence; SEQ ID NO: 14) is designed to hybridize to non-hypermutated sequences (GG), and the "hypermutated" probe (designated F', a mutated viral sequence; SEQ ID NO: 17) is designed to hybridize to the hypermutated version of the same sequence (AA). The two probes may be labeled with distinct fluorophores and compete for the same binding location on the DNA. When an exact match occurs, a fluorescent signal can be detected. When base mismatches (designated *) are present, the probe does not bind and the fluorophore is quenched by the quencher (Q). Depending on which fluorescent signal is seen (F or F'), the sequence can be identified as either hypermutated (SEQ ID NO: 16) or intact (SEQ ID NO: 15).

FIG. 7. Comparison of full-length genomes from different patient groups indicates rapid accumulation of defective proviruses. Three different patients groups are shown along with the number of patients and proviral clones studied for each group (representative sequences shown in FIG. 5). In addition, proviral clones were analyzed from an in vitro experiment, following a single round of replication (FIG. 6). Defective proviruses were identified following a single round of replication and were found at high levels in each of the three patient populations. Sequence deletions were the most common defect and were identified in all groups. Deletions encompassing all or part of the gag gene are labeled as 5' end deletions and deletions encompassing all or part of the env gene are labeled as 3' end deletions. Deletions encompassing both regions are labeled as very large internal deletions. Hypermutation was observed in all groups with significantly higher levels in acutely treated patients compared with other groups. The data is summarized in table 1, infra.

DETAILED DESCRIPTION

Overview

Figure 1:
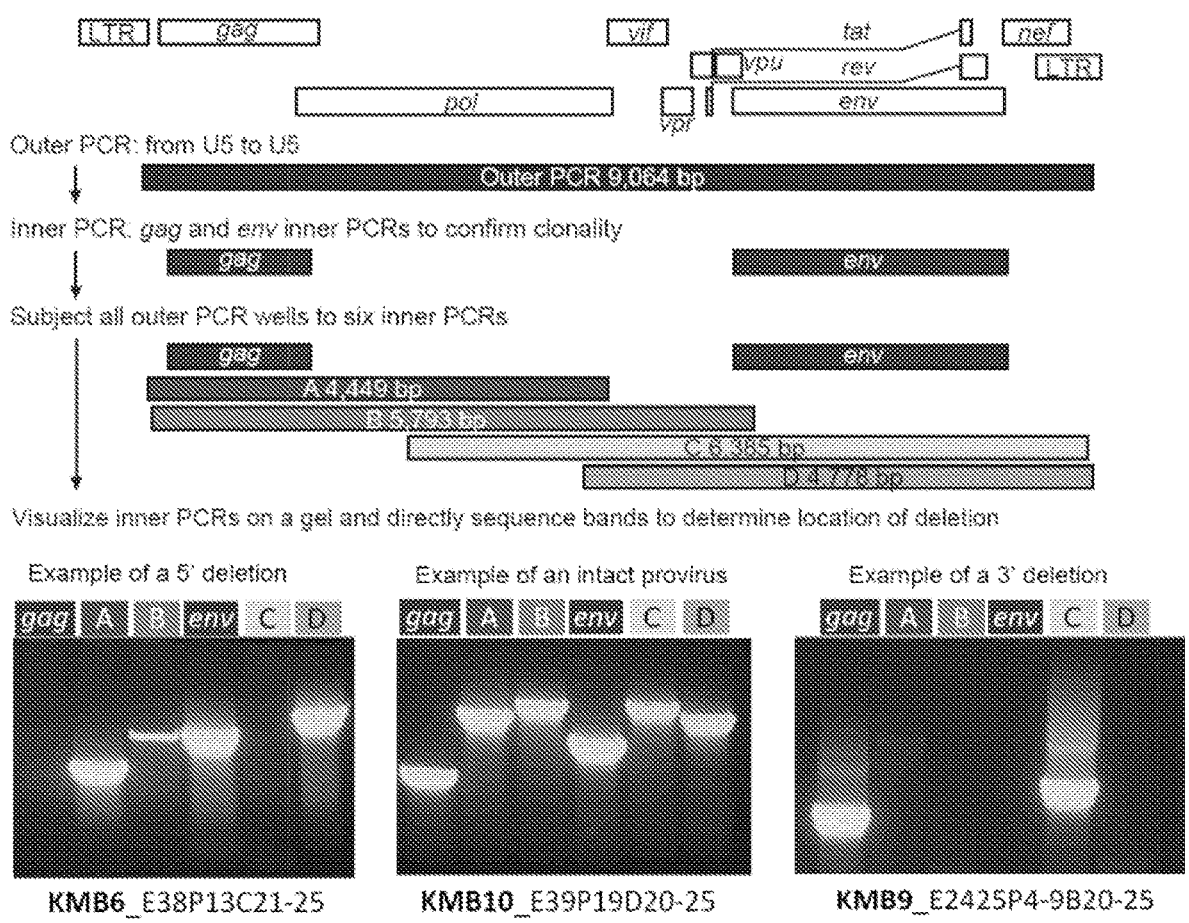
FIG. 1. Schematic of full-length proviral genome analysis. Resting CD4+ T cells are isolated from HIV-1 positive patient blood and the DNA is extracted. Nested PCRs are performed at limiting dilution and gag and env PCRs are used to determine clonality. Once a clonal dilution has been established, all PCR wells are subjected to 6 inner PCRs and visualized on a gel. The bands are extracted and directly sequenced. Near full-length proviral genomes are reconstructed using the six overlapping inner PCRs and sequences are evaluated for defects.

Many proviruses contain deletions that impair viral replication, and current assays fail to detect each of the most common deletions. Thus, proviral sequences were examined from a cohort of 9 chronically infected HIV-1 infected individuals, 7 acutely infected individuals and 2 viremic (infected but untreated) individuals, using a limiting dilution nested PCR method, as described in the Examples section. Proviral genomes were directly sequenced from the PCR products and analyzed for different defects. Out of 133 proviruses sequenced in the chronically treated cohort, only 5 integrated HIV-1 genomes were completely genetically intact with no discernable defects. Large sequence deletions were the most common defect identified. These deletions were observed in 117 proviruses and 73 deletions were precisely mapped by sequencing. Since some deletions encompassed forward or reverse primer binding sites for the inner PCRs, PCR amplification did not occur and exact mapping of the deletion was not possible. In these cases, the deletion size was estimated based on the locations of the primer binding sites that must have been deleted to prevent PCR amplification. Deletions were found in both the 5' and 3' ends of the HIV genome and some deletions encompassed large central portions of the genome. A similar analysis was conducted for the acute patient cohort and out of the 110 sequences identified, only 11 integrated HIV-1 genomes were completely genetically intact with no discernable defects. Large sequence deletions and hypermutation were the most common defects, comprising 90% of all the sequences. Viremic patients also had a substantial percentage of defective proviruses with over 65% of all sequences containing defects. In all of these types of deletions, regions of sequence homology were commonly found on both junctions of the deletion and are consistent with the proposed mechanism of a single polymerase jump by reverse transcriptase during reverse transcription resulting in the deletion of the intervening sequence. These sequence deletions generally encompassed larger than 3 kb of the 10 kb genome, thus these proviruses are incapable of making many of the proteins necessary for replication. To develop an assay to measure the LR, all of the different locations where large sequence deletions often occur were identified.

Additionally, many proviruses contain mutations that impair viral replication, and current assays fail to detect such mutations. For example, APOBEC3G is a human anti-viral defense protein that blocks HIV-1 replication by generating extensive G→A mutations in the infecting HIV-1 genome. APOBEC3G-induced G→A hypermutation was the second most common defect in the chronically treated patients and 21 proviruses were identified as hypermutated. Hypermutation was even more pronounced in the acutely treated patient cohort, with ~40% of all sequences containing hypermutation defects. The hypermutation was extensive in all sequences and was found throughout the genome. These G→A nucleotide substitutions resulted in a number of in-frame STOP codons, thus these HIV-1 genomes are nonfunctional and cannot replicate. Twelve of these hypermutated genomes in the chronically treated patients and 18 in the acutely treated patients also had large sequence deletions indicating that the hypermutation and deletion processes can occur independently. A small subset of sequences (5 proviruses in the chronically treated patients and 1 in the acutely treated patients) contained small deletions in the packaging signal of the genome. Without this region intact, the RNA genome is not packaged into the virions properly and the virus cannot replicate. Thus, these viruses should also be considered defective.

Figure 2:
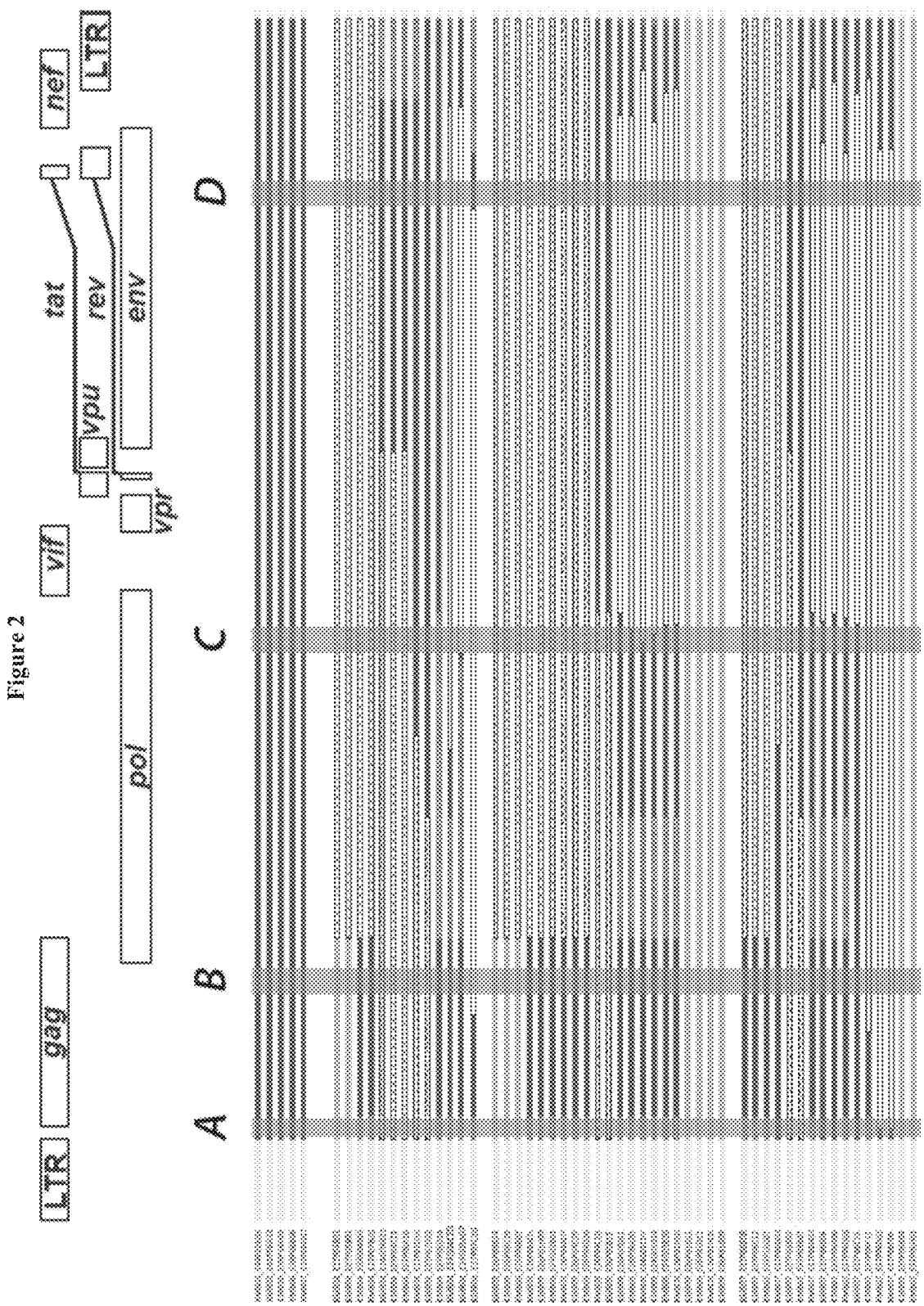
FIG. 2. Proviruses in patient resting CD4+ T cells are overwhelmingly defective yet commonly detected by PCR methods using a single primer/probe set. Proviral sequences from nine chronically-treated HIV-1 infected individuals were analyzed using a limiting dilution nested PCR method. PCR products were directly sequenced and proviral genomes were analyzed for different defects. 133 total sequences were identified and the majority were defective. Only five genomes were completely genetically intact with no discernable defects. Large sequence deletions in either the 5' or the 3' end of the genome were observed in 115 proviruses and 73 were precisely mapped by sequencing. Four different regions commonly measured via PCR using a single primer/probe set are shown and include the gag (shown in B), pol (C) and env (D) genes along with the packaging signal region (A). These PCR methods detect primarily defective proviruses. A prophetic combinatorial approach is shown (A-D) in which only proviruses that are positive for all PCRs A-D are considered intact. If hypermutation specific probes are also added (A-D+hyp. specific probes) to distinguish hypermutated sequences from intact, only primarily intact genomes are measured and there are no false positives.
Figure 2:
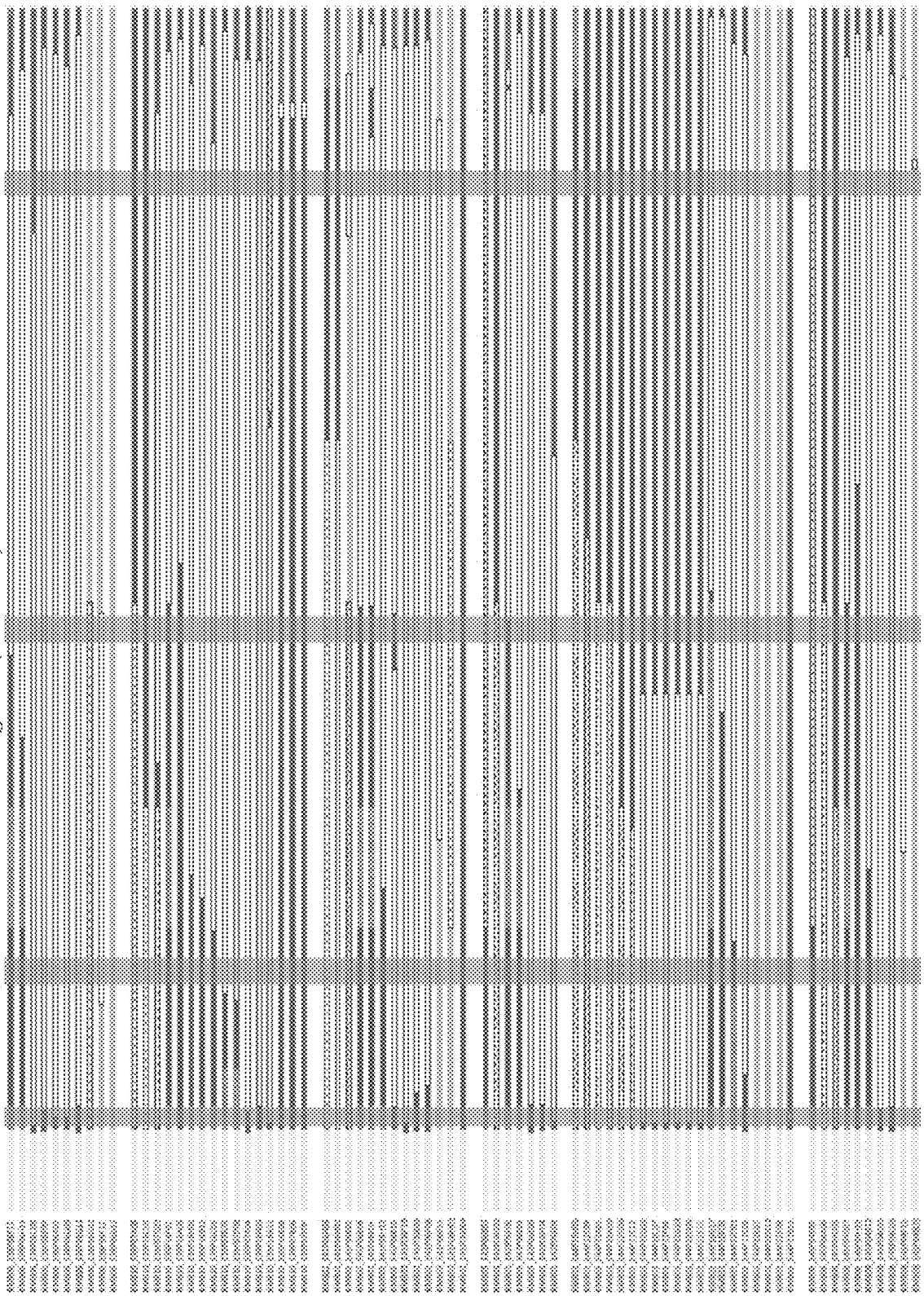
Figure 2:
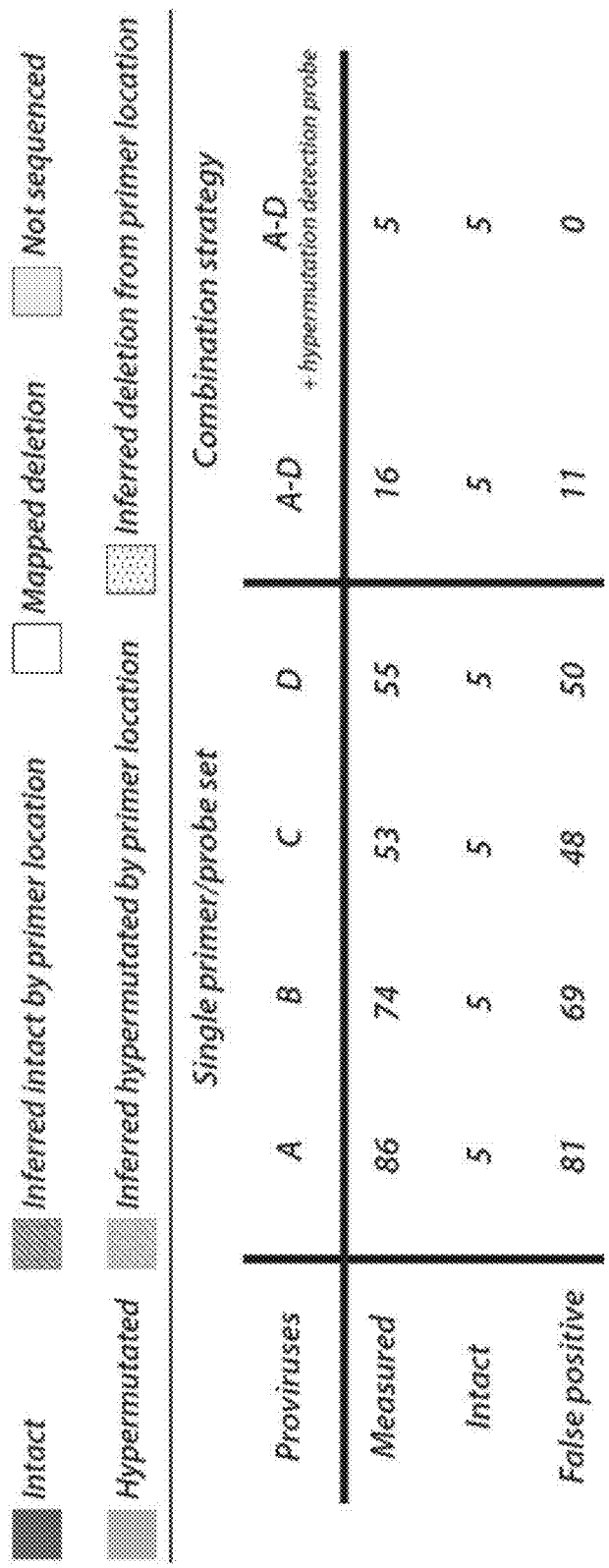

Based on the unbiased screening of proviruses to characterize the location and type of defects found in HIV-1 proviruses, a more accurate method for measuring the LR was developed. These results indicate that proviral defects can be located throughout the HIV-1 genome, thus a more complex strategy is required to distinguish them from intact proviruses. These findings expand the library of proviral defects, particularly the large sequence deletions that had previously only been shown to occur on the 3' end of the genome. Since current PCR assays only measure in one location, it was not previously possible to determine if proviruses measured from such methods are actually intact or defective. Thus, the results from the disclosed screens permit the mapping of common defects and the identification of proviruses that contain such defects. By probing the HIV-1 genome in multiple regions found to be most commonly defective, defective proviruses can be distinguished from those that are intact (FIG. 2).

Strategy for Measuring the Latent Reservoir in a Subject

Since intact proviruses make up only ~4% of all proviruses in chronically treated patients and ~10% in acutely treated patients, it is important to have an accurate methods to distinguish them from the overwhelming number of defective proviruses. Large sequence deletions make up over 80% of all proviruses and can be distinguished from intact proviruses through the use of multiple primer/probe sets. These sets are located in conserved regions of the packaging signal, gag, pol and env genes and minimize the impact of HIV-1 patient-to-patient sequence variability on measurement accuracy. By implementing measurements in these key regions where almost all sequence deletions are located, only proviruses that give a positive probe fluorescent signal in all locations are measured as intact.

APOBEC3G induced G→A hypermutation is the second most commonly found defect, thus it is important that these types of proviruses be distinguished from genetically intact proviruses. About half of hypermutated sequences in both the acutely and chronically treated cohorts do not have any deletions and cannot be distinguished from intact proviruses by simply measuring in multiple locations. To specifically distinguish between hypermutated and intact sequences, we developed preferentially binding nucleotide probes. The probes are designed to hybridize to a region of DNA that is commonly hypermutated in patient sequences. The "intact" probe is designed to hybridize to the non-hypermutated sequence (GG), and the "hypermutated" probe is designed to hybridize to the hypermutated sequence (AA). The two probes are labeled with distinct fluorophores and compete for the same binding location on the DNA. The one that matches the DNA binds and gives a distinct fluorescent signal and the other does not (FIG. 4), in a similar manner to allelic discrimination probes that are used to detect single nucleotide polymorphisms (SNPs). These probes are specific for different intact and hypermutated sequences, as demonstrated in vitro. These hypermutation probes can be used at one or more of the described regions (A-D) to distinguish hypermutated from intact sequences and improve the accuracy of the assay (FIG. 2).

Figure 3:
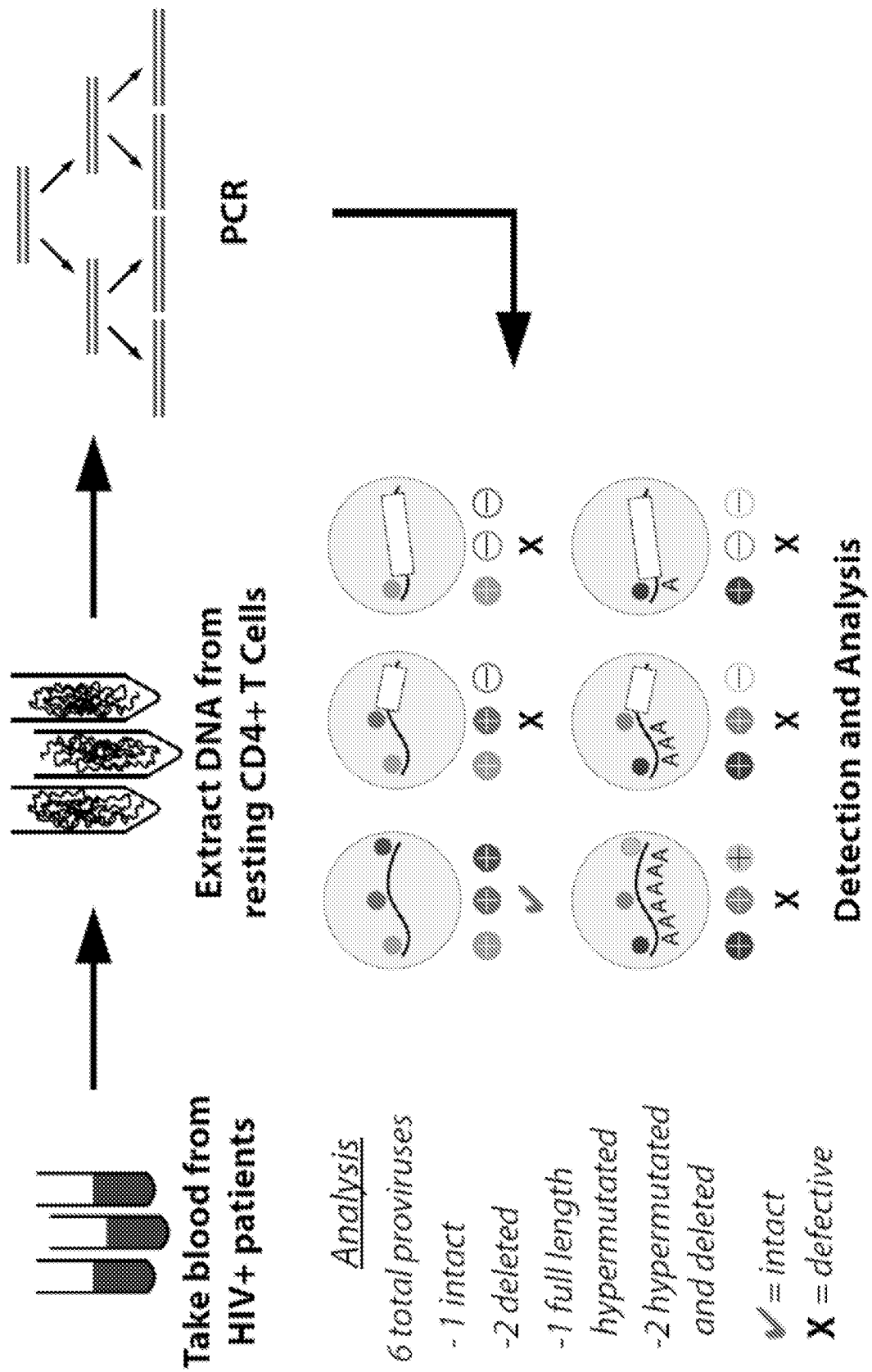
FIG. 3. Method for determining whether nucleic acids in a sample obtained from CD4+ T cells comprise intact HIV-1 proviruses. Muliplex PCR is performed on DNA from purified resting CD4+ T cells (or other cell population). Three or four primer/probe sets are used to amplify regions of the genome that are commonly defective. For some sets of primers, two different fluorescent probes are used, one specific for non-hypermutated sequences and one specific for G→A hypermutated sequences. Fluorescence is evaluated for each provirus, providing a rapid and precise quantitation of the fraction of proviruses that are intact and the fraction that have various types of defects.

An assay that can distinguish intact proviruses from defective ones is a top HIV-1 cure research priority. Based on the results of HIV-1 proviral genome analysis, a new and accurate method for measuring the LR was developed. A workflow of the method is shown in FIG. 3 and it can be applied to a variety of cells types that are thought to potentially harbor HIV-1 genomes, including but not limited to lymphocytes, macrophages, and hematopoietic progenitor cells. The principles described in this assay can also be applied to animal models of HIV-1 infection, including those that the closely related simian retrovirus SIV or SIV-HIV hybrid retroviruses. Through measuring the HIV-1 genome in multiple regions and including probes that specifically distinguish hypermutated from intact genomes, intact, potentially replication-competent proviruses can be identified, which must be eliminated to cure HIV-1.

Methods for Determining Whether a Nucleic Acid Comprises an Intact Virus or Provirus In some aspects, the invention relates to a method for determining whether a nucleic acid comprises an intact virus or provirus. The nucleic acid may be DNA (e.g., from a provirus) or RNA (e.g., from a virus). The method may optionally comprise amplifying the nucleic acid with PCR primers that amplify a plurality of conserved nucleotide sequences of the provirus. The method may optionally comprise amplifying the nucleic acid in a PCR reaction comprising at least one PCR primer or probe comprising a native viral sequence, wherein the at least one PCR primer or probe comprising a native viral sequence has a higher binding affinity for the native viral sequence than for mutated viral sequences. The method may optionally comprise amplifying the nucleic acid in a PCR reaction comprising at least one PCR primer or probe comprising a mutated viral sequence, wherein the at least one PCR primer or probe comprising a mutated viral sequence has a higher binding affinity for the mutated viral sequence than for native viral sequences. In some embodiments, the method comprises quantifying whether each PCR reaction produced a PCR product, thereby determining whether the nucleic acid comprises an intact provirus.

Methods for Measuring a Latent Viral Reservoir

In some aspects, the invention relates to methods of measuring a latent viral reservoir in a subject. The method may comprise obtaining a sample of nucleic acids of the subject; amplifying the nucleic acids of the sample with PCR primers that amplify a plurality of conserved nucleotide sequences of the virus; and quantifying the frequency at which each nucleotide sequence of the plurality occurs in the same nucleic acid in the sample, thereby measuring the latent viral reservoir in the subject.

In some embodiments, the method comprises amplifying the nucleic acids in a PCR reaction comprising a first at least one PCR primer or probe comprising a native viral sequence, wherein the first at least one PCR primer or probe has a higher binding affinity for native viral sequences than for mutated viral sequences. The first at least one PCR primer or probe may comprise a primer, such as a primer used to amplify the plurality of conserved nucleotide sequences. In some embodiments, the first at least one PCR primer or probe is not a primer used to amplify the plurality of conserved nucleotide sequences. In some embodiments, the first at least one PCR primer or probe comprises a qPCR probe.

In some embodiments, the method comprises amplifying the nucleic acids in a PCR reaction comprising a second at least one PCR primer or probe comprising a mutated viral sequence, wherein the second at least one PCR primer or probe has a higher binding affinity for mutated viral sequences than for native viral sequences. In some embodiments, the second at least one PCR primer or probe comprises a primer. In some embodiments, the second at least one PCR primer or probe comprises a qPCR probe.

In some embodiments, the second at least one PCR primer or probe binds to a mutated viral sequence that is related to a native viral sequence that a first at least one PCR primer binds, wherein the mutated viral sequence consists of the native viral sequence comprising at least one mutation. For example, the mutated viral sequence may consist of the native viral sequence to which at least 1, 2, 3, 4, 5, 6, 7, 8, 9, or 10 mutations have been made. The mutations may comprise, for example, a guanine to adenine mutation.

In some embodiments of the invention, a PCR probe is used to detect either a native viral sequence or a mutated viral sequence. A PCR probe used to detect a native viral sequence may be used in conjunction with a PCR probe used to detect a mutated viral sequence in the same PCR reaction, for example, by using probes attached to different fluorophores. A PCR probe used to detect a native viral sequence may be related to a PCR probe used to detect a mutated viral sequence by mutations to the native viral sequence, e.g., the native viral sequence may be related to the mutated viral sequence by one or more guanine to adenine mutations.

In some embodiments, the method comprises obtaining a sample of nucleic acids of the subject; amplifying the nucleic acids in a PCR reaction comprising a first at least one PCR primer or probe comprising a native viral sequence, wherein the first at least one PCR primer or probe has a higher binding affinity for the native viral sequence than for mutated viral sequences; and quantifying the frequency at which the native viral sequence occurs in the nucleic acids of the sample, thereby measuring the latent viral reservoir in the subject. The method may comprise amplifying the nucleic acid with a second at least one PCR primer or probe comprising a mutated viral sequence, wherein the second at least one PCR primer or probe has a higher binding affinity for the mutated viral sequence than for native viral sequences. The method may comprise amplifying the nucleic acids of the sample with PCR primers that amplify a plurality of conserved nucleotide sequences of the virus.

In some embodiments, the method comprises isolating each nucleic acid of the sample prior to amplifying the nucleic acids. In some embodiments, the method comprises barcoding each nucleic acid in the sample prior to amplifying the nucleic acids, e.g., by adding a unique nucleotide sequence to each nucleic acid. The method may comprise amplifying the nucleic acids with PCR primers that amplify the proviral genome, e.g., after isolating each nucleic acid and/or before amplifying a plurality of conserved nucleic acids or before amplifying a native or mutated viral sequence. The proviral genome may be amplified, for example, with PCR primers that bind to the 3' and 5' ends of the genome, such as the 3' and 5' untranslated regions.

In some embodiments, the method comprises quantifying the number of cellular nucleic acids in the sample that are analyzed. The number of nucleic acids in the sample that are analyzed may be quantified, for example, by amplifying a cellular nucleotide sequence, e.g., a genomic nucleotide sequence that is not part of the virus or provirus. The cellular nucleotide sequence may be, for example, a cellular gene, such as RNAse P.

The frequency at which each nucleotide sequence of the plurality occurs in the same nucleic acid (e.g., per total number of viral or cellular nucleic acids) may be determined by determining whether each nucleic acid comprises an intact provirus and dividing the number of nucleic acids that comprise an intact provirus by the total number of nucleic acids that are analyzed (e.g., total number of viral or cellular nucleic acids). The frequency may be determined, for example, by calculating the number of nucleic acids that comprise each nucleotide sequence of the plurality and dividing said number by the number of nucleic acids that were analyzed (e.g., total number of viral or cellular nucleic acids). The frequency of intact viruses relative to all viral sequences in the sample may be determined, for example, by dividing the number of intact viruses by the total number of nucleic acids that contain viral DNA. The frequency of intact viruses relative to the number of cells probed may be determined, for example, by dividing the number of intact viruses by the total number of nucleic acids that contain a cellular nucleotide sequence, such as a cellular gene (e.g., RNAse P).

In some embodiments, the invention relates to methods of measuring the frequency of replication incompetent proviruses in a viral reservoir in a subject. The frequency may be determined, for example, by calculating the number of nucleic acids that do not comprise each nucleotide sequence of the plurality and dividing said number by the number of nucleic acids that were analyzed (e.g., the total number of viral nucleic acids or the total number of cellular nucleic acids).

Determining Whether a Nucleic Acid Comprises an Intact Provirus

A nucleic acid may be found to comprise an intact provirus if each PCR reaction that amplifies a conserved nucleotide sequence of the provirus, if any such reactions were performed, indicates that the nucleic acid comprises each conserved nucleotide sequence. Similarly, the nucleic acid may be found to comprise an intact provirus if each PCR reaction performed with a PCR primer or probe comprising a native viral sequence indicates that the nucleic acid comprises the native viral sequence. Similarly, the nucleic acid may be found to comprise an intact provirus (e.g., a non-mutated provirus) if each PCR reaction performed with a PCR primer or probe comprising a mutated viral sequence indicates that the nucleic acid lacks the mutated viral sequence.

A PCR reaction may be analyzed, for example, by performing qPCR or ddPCR and analyzing a fluorescent readout. Similarly, a PCR reaction may be analyzed by quantifying the amount of a PCR product, for example, by UV-Vis spectroscopy, by quantifying the amount of PCR product by electrophoresis/densitometry, or by sequencing the PCR product.

Determining the Proportion of Intact, Hypermutated, Deleted, or Defective Proviruses in a Sample In some aspects, the invention relates to a method for determining the proportion of intact, hypermutated, deleted, and/or defective proviruses in a sample of nucleic acids. The sample may be obtained from a subject (e.g., a human subject) either directly (e.g., by drawing blood or by taking a biopsy) or indirectly (e.g., from a care provider or archive).

The method may comprise amplifying the nucleic acids with at least one PCR primer or probe comprising a native viral sequence, wherein each of the at least one PCR primer(s) or probe(s) comprising a native viral sequence has a higher binding affinity for the native viral sequence than for mutated viral sequences. The method may comprise, for example, amplifying the nucleic acids with PCR primers or probes comprising 1, 2, 3, 4, 5, 6, 7, 8, 9, 10, 11, 12, 13, 14, 15, 16, 17, 18, 19, 20, or more native viral sequences. For retroviruses, such as HIV, a native viral sequence may comprise, for example, a nucleotide sequence encoding all or part of a viral packaging signal, Gag, Pol, Env, Tat, Nef, Rev, Vif, Vpr, Vpu, and/or one or more long-terminal repeats (LTRs). Thus, the 1, 2, 3, 4, 5, 6, 7, 8, 9, 10, 11, 12, 13, 14, 15, 16, 17, 18, 19, 20, or more native viral sequences may comprise nucleotide sequences encoding all or part of a viral packaging signal, Gag, Pol, Env, Tat, Nef, Rev, Vif, Vpr, Vpu, and/or one or more LTRs, including nucleotide sequences that overlap with the nucleotide sequences of other PCR primers or probes.

The method may comprise amplifying the nucleic acids with at least one PCR primer or probe comprising a hypermutated viral sequence, wherein each of the at least one PCR primer(s) or probe(s) comprising a hypermutated viral sequence has a higher binding affinity for the hypermutated viral sequence than for native viral sequences. The method may comprise, for example, amplifying the nucleic acids with PCR primers or probes comprising 1, 2, 3, 4, 5, 6, 7, 8, 9, 10, 11, 12, 13, 14, 15, 16, 17, 18, 19, 20, or more hypermutated viral sequences. For retroviruses, such as HIV, a hypermutated viral sequence may comprise, for example, a nucleotide sequence with less than 100% sequence identity to a nucleotide sequence encoding all or part of a viral packaging signal, Gag, Pol, Env, Tat, Nef, Rev, Vif, Vpr, Vpu, and/or one or more LTRs, but more than 20%, 25%, 30%, 35%, 40%, 45%, 50%, 55%, 60%, 65%, 70%, 75%, 80%, 85%, 90%, or 95% sequence identity to one of the aforementioned sequences and/or occurring at a location in the genome of the provirus corresponding to one of the aforementioned sequences (see, e.g., FIGS. 1, 2, and 5 for maps of the HIV-1 provirus). For example, a hypermutated viral sequence may vary from a nucleotide sequence encoding all or part of a viral packaging signal, Gag, Pol, Env, Tat, Nef, Rev, Vif, Vpr, Vpu, and/or one LTRs by a number of guanine to adenine mutations.

The method preferably comprises quantifying the amount of each PCR product that was produced, e.g., by quantitative PCR ("qPCR"), droplet digital PCR ("ddPCR"), or by electrophoresis.

The method may comprise calculating the proportion of intact proviruses in the sample, e.g., by dividing the number of nucleic acids in the sample that comprise each native viral sequence, but that comprise no hypermutated viral sequence, by the number of nucleic acids in the sample that comprise any viral sequence.

The method may comprise calculating the proportion of hypermutated proviruses in the sample, e.g., by dividing the number of nucleic acids in the sample that comprise any hypermutated viral sequence by the number of nucleic acids in the sample that comprise any viral sequence.

The method may comprise calculating the proportion of deleted proviruses in the sample, e.g., by dividing the number of nucleic acids in the sample that comprise any viral sequence, but that comprise less than each native viral sequence, by the number of nucleic acids in the sample that comprise any viral sequence.

The method may comprise calculating the proportion of defective proviruses in the sample, e.g., by dividing the number of nucleic acids in the sample that comprise any hypermutated viral sequence and/or less than each native viral sequence by the number of nucleic acids in the sample that comprise any viral sequence.

In preferred embodiments, the method further comprises isolating each nucleic acid in the sample prior to amplifying the nucleic acids, e.g., by ddPCR. Nevertheless, some embodiments of the invention do not require the isolation of each nucleic acid.

Types of Viruses and Mutations

The virus may be a retrovirus, such as a lentivirus. For example, the virus may be HIV, such as HIV-1 or HIV-2. The plurality of conserved viral nucleotide sequences may be selected from nucleotide sequences that encode a viral packaging signal, Gag, Pol, Env, Tat, Nef, Rev, Vif, Vpr, Vpu, and/or one or more long-terminal repeats (LTRs).

A mutated viral sequence may comprise at least one guanine to adenine mutation, such as at least 2, 3, 4, 5, 6, 7, 8, 9, or even 10 guanine to adenine mutations. A hypermutated provirus may comprise at least 10, 50, 100, 200, or more mutations, and thus, a hypermutated provirus may comprise many different mutated viral sequences that may be assayed with different PCR primers and probes.

Subjects and Samples

The subject may be a multicellular organism, such as a plant or animal. The subject may be a vertebrate, such as a fish, amphibian, reptile, bird, or mammal. The subject may be a murine, canine, feline, ovine, porcine, bovine, equine, or primate. For example, the subject may be a human.

The sample may be obtained directly from a subject, such as by drawing blood from the subject or performing a biopsy. The sample may be obtained indirectly, for example, from the subject's physician or from an archive. The nucleic acids of the sample may be obtained from peripheral blood mononuclear cells, such as lymphocytes. The nucleic acids of the sample may be obtained from T cells, such as resting T cells. The nucleic acids of the sample may be obtained from CD4+ T cells, such as resting CD4+ T cells.

The sample may be from a human subject with HIV. The subject may be viremic, acutely-treated, or chronically treated. In some embodiments, the subject is acutely-treated or chronically treated with antiretroviral therapy ("ART"), combination anti-retroviral therapy ("cART"), or highly active antiretroviral therapy ("HAART"). In some embodiments, the sample is from a subject (e.g., a human subject), and the subject does not have HIV.

Kits for Determining Whether a Nucleic Acid Comprises an Intact Provirus

In some aspects, the invention relates to a kit for determining the proportion of intact, hypermutated, deleted, and/or defective proviruses in a sample of nucleic acids, comprising at least one PCR primer or probe comprising a native viral sequence, wherein each of the at least one PCR primer(s) or probe(s) comprising a native viral sequence has a higher binding affinity for the native viral sequence than for mutated viral sequences; and at least one PCR primer or probe comprising a hypermutated viral sequence, wherein each of the at least one PCR primer(s) or probe(s) comprising a hypermutated viral sequence has a higher binding affinity for the hypermutated viral sequence than for native viral sequences. The provirus may be a lentivirus, such as provirus is HIV. The native viral sequences may be selected from nucleotide sequences that encode all or part of a viral packaging signal, Gag, Pol, Env, Tat, Nef, Rev, Vif, Vpr, Vpu, and/or one or more long-terminal repeats (LTRs). The hypermutated viral sequences may be selected from nucleotide sequences that vary from nucleotide sequences that encode all or part of a viral packaging signal, Gag, Pol, Env, Tat, Nef, Rev, Vif, Vpr, Vpu, and/or one or more long-terminal repeats (LTRs) by one or more mutations, such as guanine to adenine mutations. The kit may further comprise PCR primers that amplify substantially all of the provirus; for example, the kit may comprise PCR primers that bind to the 3' and 5' ends of the provirus.

This disclosure will be better understood from the Experimental Details which follow. However, one skilled in the art will readily appreciate that the specific methods and results discussed are merely illustrative of the disclosure as described more fully in the embodiments which follow thereafter.

EXEMPLIFICATION

Example 1—Analysis of Latent Viral Reservoirs in Human Subjects with Undetectable Plasma HIV-1 RNAs Level for at Least 1 Year Study Subjects HIV-1-infected individuals were enrolled in the study based on the criteria of suppressive ART and undetectable plasma HIV-1 RNAs level (<50 copies per mL) for a minimum of 1 year.

Isolation of Resting CD4+ T Lymphocytes

PBMCs from whole blood were isolated using density centrifugation on a Ficoll-Hypaque gradient. CD4+ T cells were isolated from PBMCs using a negative selection method (CD4+ T cell Isolation Kit II, Miltenyi Biotec). Resting CD4+ lymphocytes (CD4+, CD69−, CD25− and HLA-DR−) were further enriched by a second negative depletion (CD25-Biotin, Miltenyi Biotec; Anti-Biotin MicroBeads, Miltenyi Biotec; CD69 MicroBead Kit II, Miltenyi Biotec; Anti-HLA-DR MicroBeads, Miltenyi Biotec). Aliquots of $2\times10^6$ resting CD4+ cells were frozen viably at −80° C. until the time of DNA extraction. Resting CD4+ cell purity was verified using flow cytometry.

DNA Extraction and Limiting Dilution PCR

DNA was extracted from $2\times10^6$ resting CD4+ cells using the Qiagen Gentra Purgene Cell Kit A and was subjected to nested limiting dilution PCR. The outer PCR was nearly full-length from U5 to U5, followed nested amplification of both gag and env to determine clonality. Aliquots from each clonal (p>0.85) outer PCR well, regardless if they were positive and negative for gag and env, were subjected to six inner PCRs. PCR products were visualized on a 1% agarose gel and the products directly sequenced to obtain near full-length genome sequences. Control experiments were performed using the reference genome NL4-3 and no defects (deletions or hypermutation) were observed. Primers were used as described by Ho, Y.-C. et al. (Cell 155:540-551 (2013).

Analysis

All sequences were aligned and compared to the reference genome HXB2 to determine defects such as large sequence deletions. Hypermutation was determined using the Los Alamos Hypermut2 algorithm (Rose, P. P. and Korber, B. T., *Bioinformatics* 16:400-401(2000)).

Resting CD4+ T cells are isolated from HIV-1 positive patient blood and the DNA is extracted. Nested PCRs are performed at limiting dilution and gag and env PCRs are used to determine clonality. Once a clonal dilution has been established, the PCR wells are subjected to 6 inner PCRs and visualized on a gel (FIG. 1). The bands are extracted and directly sequenced. Full length proviral genomes are reconstructed using the six overlapping inner PCRs and sequences are evaluated for large sequence deletions and hypermutation.

Nine chronically treated patients, seven acutely treated patients, and two viremic (infected, but untreated) patients were analyzed in this study and large sequence deletions were found by direct sequencing of PCR products (FIG. 2). Deletions were found in both the 5' and 3' ends of the HIV genome in all patient groups and some deletions encompassed large portions of both ends. Out of the 133 sequences identified and sequenced in the chronically treated group, deletions were directly mapped in 73 proviral sequences. Since some deletions encompassed forward or reverse primer binding sites, PCR amplification did not occur and direct mapping of the deletion was not possible. A similar analysis was conducted for the acute patient cohort and large sequence deletions and hypermutation were the most common defects, comprising 90% of all the sequences. Viremic patients also had a substantial percentage of defective proviruses with over 65% of all sequences containing defects. Only 5 genetically intact sequences were identified (<5% of total sequences) in the chronically treated patients and 11 sequences (10%) in the acutely treated patients.

Figure 6:
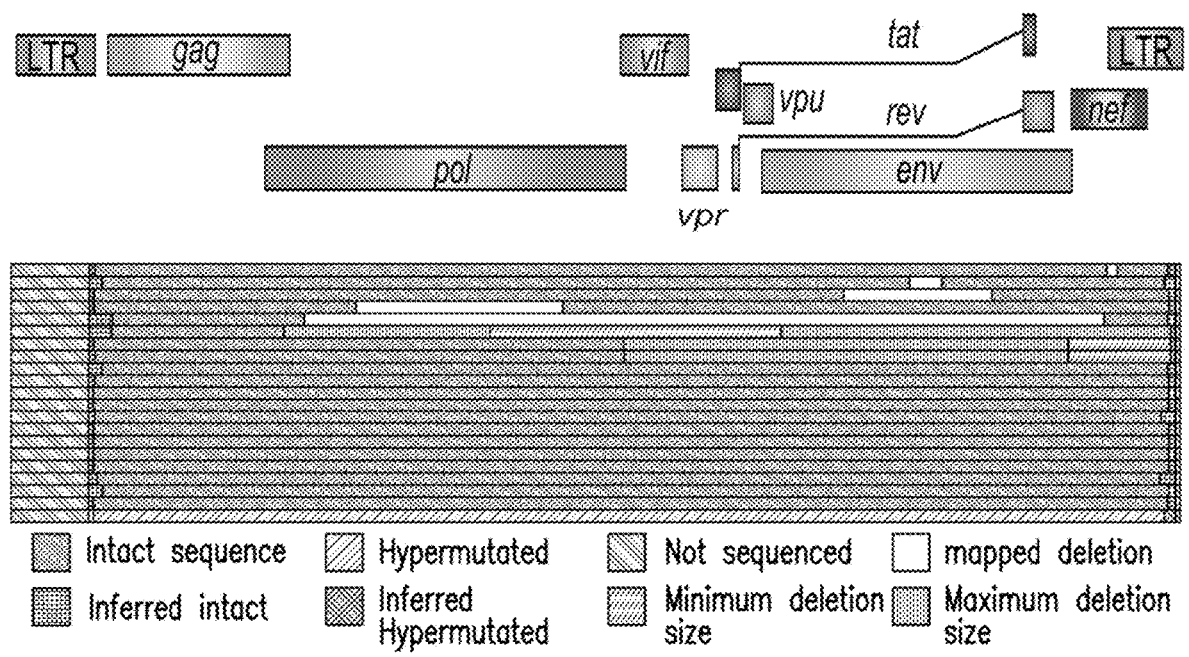
FIG. 6. Defective proviruses are readily detected following a single round of reverse transcription. Activated CD4+ T cells were infected with BaL virus and T20 was added following infection to block additional rounds of infection. The method in FIG. 1 was used to evaluate presence or absence of genomic sequence defects. Defective proviruses were readily detected, although there was a higher fraction of intact proviruses compared to what previously has been seen in chronically-treated patients. Some deletions encompassed forward or reverse primer binding sites, thus PCR amplification did not occur and direct mapping of the deletion was not possible. The maximum and minimum sizes of these deletions were estimated using the primer locations of the inner PCRs that did and did not amplify.

Example 2—Detection of Defective Proviruses Following a Single Round of Reverse Transcription Activated CD4+ T cells were infected with BaL virus and T20 was added following infection to block additional rounds of infection. The above method was used to evaluate presence or absence of genomic sequence defects. Defective proviruses were readily detected (FIG. 6). Some deletions encompassed forward or reverse primer binding sites, thus PCR amplification did not occur and direct mapping of the deletion was not possible. The maximum and minimum sizes of these deletions were estimated using the primer locations of the inner PCRs that did and did not amplify.

Figure 5A:
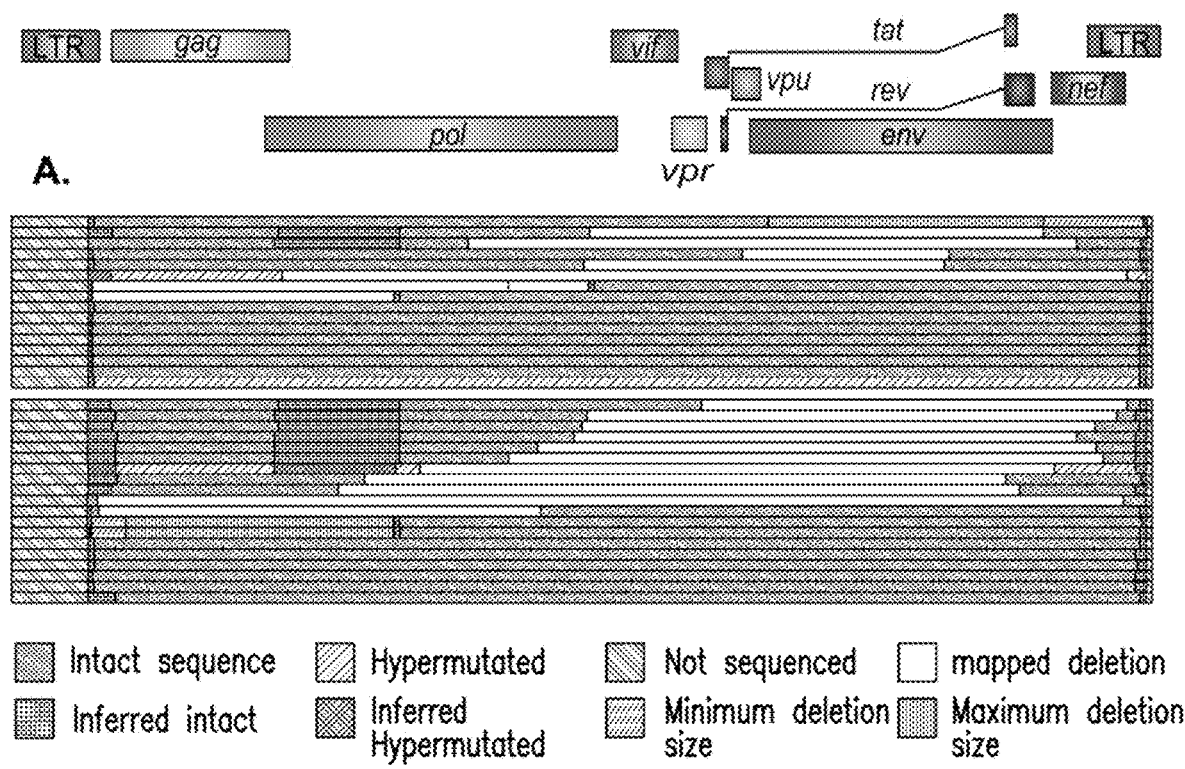
FIG. 5. The majority of sequences are defective in viremic patients (A) and in patients treated during either chronic (B) or acute (C) infection. Sequences from representative patients from each group are shown. The two most common defects were large sequence deletions and APOBEC3G hypermutation. Deletions were found in both the 5' and 3' ends of the HIV genome and some deletions encompassed large portions of both ends. In some cases, a mapped deletion encompassed the primer binding sites for other inner PCRs, thus a region of sequence was not captured but is presumed to be present. These regions are denoted by a shaded region of black (intact) or dark grey (hypermutated). Some deletions encompassed forward or reverse primer binding sites, thus PCR amplification did not occur and direct mapping of the deletion was not possible. In these cases the maximum (medium gray) and minimum (light gray) sizes of these deletions were estimated using the primer locations of the inner PCRs that did and did not amplify.
Figure 5B:
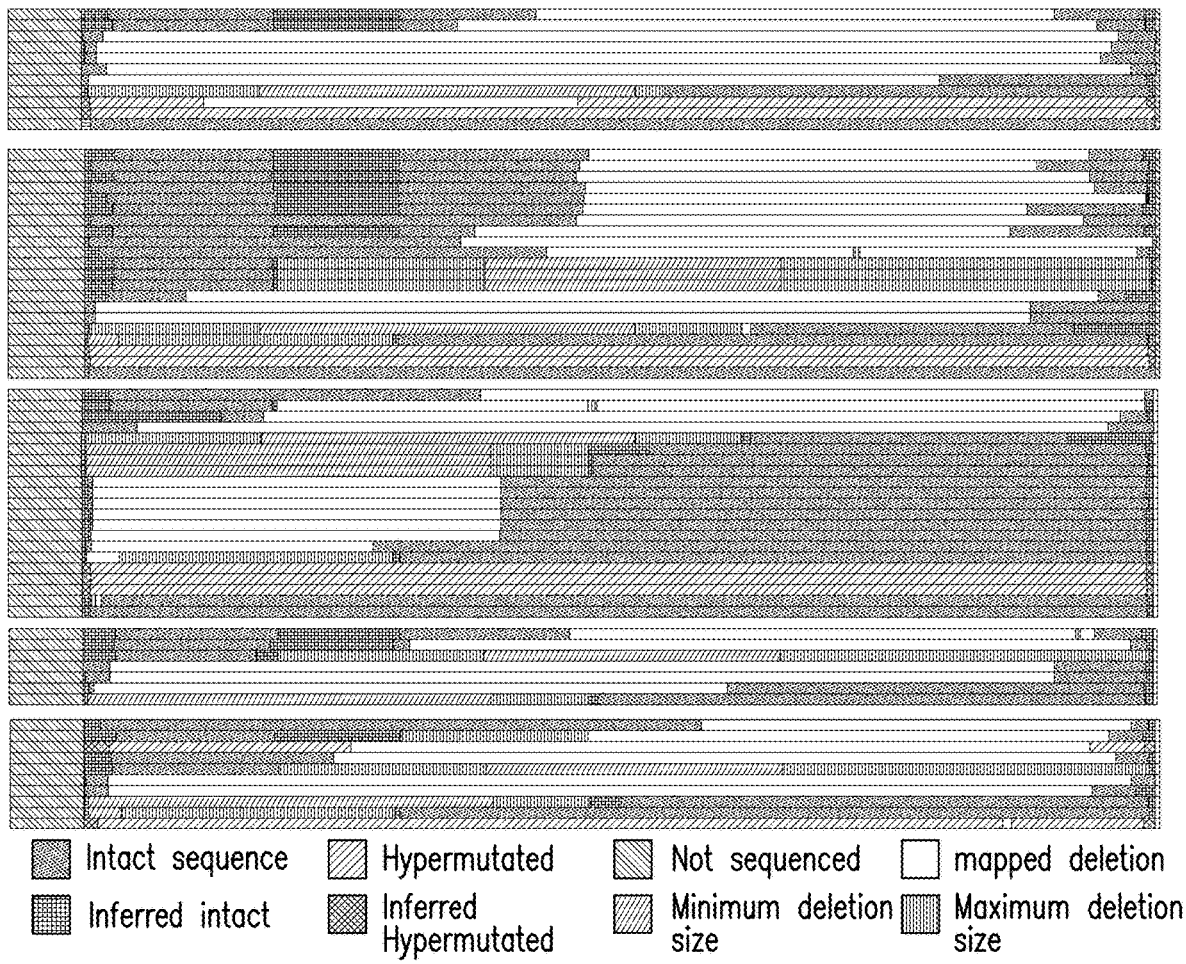
Figure 5C:
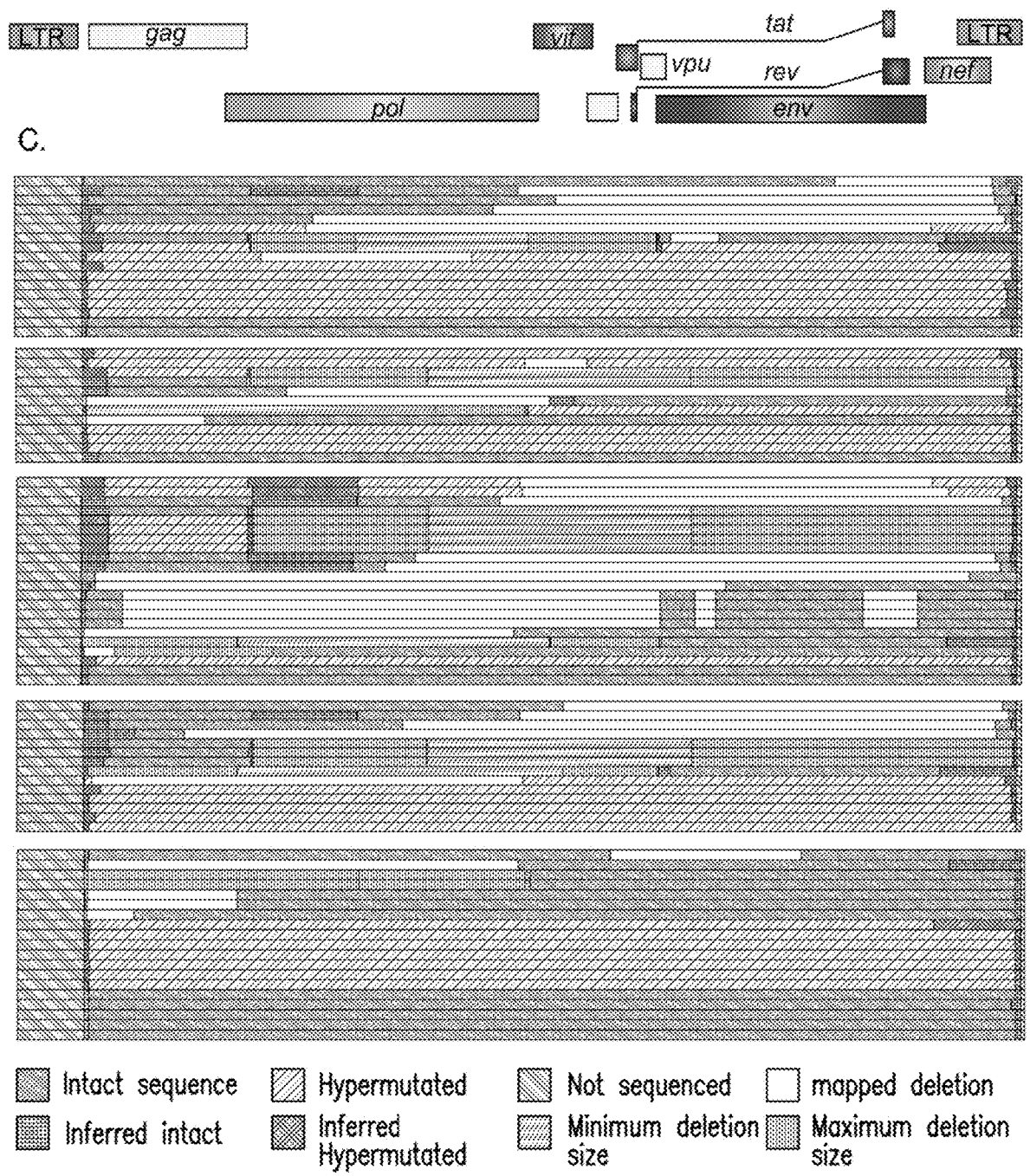

Example 3—Proportion of Intact, Hypermutated, and Deleted Proviruses in the Latent Proviral Reservoirs of Various Patient Subgroups The latent proviral reservoirs for three patient subgroups were assessed as described in example 1, supra, including two viremic patients, seven acutely treated patients, and nine chronically treated patients. Representative sequences for each patient subgroup are shown in FIG. 5. The two most common defects were large sequence deletions and APOBEC3G hypermutation. Deletions were found in both the 5' and 3' ends of the HIV genome and some deletions encompassed large portions of both ends. In some cases, a mapped deletion encompassed the primer binding sites for other inner PCRs, and thus a region of sequence was not captured but was presumed to be present. Some deletions encompassed forward or reverse primer binding sites, and thus PCR amplification did not occur, and direct mapping of the deletion was not possible.

Defects were found at high levels in each of the three patient populations. Sequence deletions were the most common defect and were identified in all groups (Table 1; FIG. 7). Deletions encompassing all or part of the gag gene were labeled as 5' end deletions and deletions encompassing all or part of the env gene are labeled as 3' end deletions. Deletions encompassing both regions were labeled as very large internal deletions. Hypermutation was observed in all groups with significantly higher levels in acutely treated patients compared with other groups.

Proviruses in chronically treated patients were overwhelmingly defective, with less than 5% of sequences being genetically intact. Proviruses in acutely treated patients displayed more hypermutation than those in chronically treated patients, likely from high APOBEC activity during acute infection. The high percentage of defective proviruses in acutely treated patients suggests that defective proviruses accumulate rapidly, early in the course of infection. Viremic patients, in whom most cells are recently infected, had a significantly higher fraction of intact proviruses.

Additionally, proviral clones analyzed in the in vitro experiment described in Example 2, were compared with the three patient subgroups (Table 1; FIG. 7).

In certain embodiments, known PCR probes and primers may be used to assay and/or amplify a nucleotide sequence according to the specification. Various methods of the invention may be performed with any number of different PCR probes and/or primers that recognize native viral nucleotide sequences and/or mutated viral nucleotide sequences.

PCR primers and probes used to detect a HIV-1 packaging signal:

```
Forward Primer 5PackF1
                                  SEQ ID NO: 1
TCT CTC GAC GCA GGA CTC Reverse Primer 3PackR1
                                  SEQ ID NO: 2
TCT AGC CTC CGC TAG TCA AA Probe Pack1 (IDT's Zen/3'IBFQ)
                                  SEQ ID NO: 3
5TET-TTT GGC GTA CTC ACC AGT CGC C
```

PCR primers and probes used to detect mutations in HIV-1

```
Forward Primer F7
                                  SEQ ID NO: 4
AGTGGTGCAGAGAGAAAAAAGAGC Reverse Prime R7
                                  SEQ ID NO: 5
GTCTGGCCTGTACCGTCAGC Hypermutated Probe hypermut4 (mutated
viral sequence)
                                  SEQ ID NO: 6
6FAM-TTCCTTAAGTTCTTAGGAGC-MGB Intact Probe normal4 (native viral sequence)
                                  SEQ ID NO: 7
VIC-CCTTGGGTTCTTGGGA-MGB
```

PCR primers and probes used to detect a HIV-1 Gag:

```
Forward Primer
                                  SEQ ID NO: 8
CAT GTT TTC AGC ATT ATC AGA AGG A Reverse Primer
                                  SEQ ID NO: 9
TGC TTG ATG TCC CCC CAC T Probe
                                  SEQ ID NO: 10
CCA CCC CAC AAG ATT TAA ACA CCA TGC TAA
```

TABLE 1

Proportion of intact, hypermutated, and deleted proviruses in various patient subgroups

| | Intact | Hypermutated | Hypermutated & Deleted | Packaging Signal Deletion | 5' Deletion | 3' Deletion | Large Internal Deletion |
|---|---|---|---|---|---|---|---|
| in vitro reverse transcription | 59% | 5% | 0% | 0% | 4% | 27% | 5% |
| Viremic patients | 35% | 3% | 5% | 0% | 19% | 35% | 3% |
| Acutely treated patients | 10% | 20% | 16% | 1% | 24% | 24% | 5% |
| Chronically treated patients | 4% | 9% | 7% | 4% | 23% | 34% | 19% |

PCR primers and probes used to detect a HIV-1 Pol:

```
Forward Primer
                                   SEQ ID NO: 11
GCA CTT TAA ATT TTC CCA TTA GTC CTA Reverse Primer
                                   SEQ ID NO: 12
CAA ATT TCT ACT AAT GCT TTT ATT TTT TC Probe
                                   SEQ ID NO: 13
VIC-AAG CCA GGA ATG GAT GGC C-MGB
```

INCORPORATION BY REFERENCE

All of the U.S. patents, U.S. published patent applications, foreign patent publications, and other publications cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

---

What is claimed is:

1. A method of detecting HIV-1 proviruses in a sample of nucleic acids from a subject, the method comprising:

obtaining the sample from the subject;

amplifying the nucleic acids with at least one PCR primer that anneals to at least a portion of a native HIV-1 proviral sequence encoding Env in the presence of at least one first probe that is specific to a hypermutated HIV-1 proviral Env sequence in the presence of at least one second probe that is specific to the native HIV-1 Env proviral sequence;

wherein the second probe is specific to the complement of SEQ ID NO: 7;

wherein the hypermutated HIV-1 proviral Env sequence is the complement of SEQ ID NO: 7 and comprises one or more APOBEC3G hypermutations;

detecting the binding of the second probe to a portion of a native HIV-1 proviral Env sequence; and amplifying the nucleic acids with at least one PCR primer that anneals to at least a portion of a native HIV-1 proviral sequence encoding a HIV-1 proviral packaging signal sequence in the presence of at least a third probe that is specific to a portion of the native HIV-1 proviral packaging signal sequence; and detecting the binding of the third probe to a portion of a native HIV-1 proviral packaging signal sequence.

2. The method of claim 1, further comprising:
amplifying the nucleic acids with at least one PCR primer that anneals to at least a portion of a native HIV-1 proviral sequence encoding Gag or
amplifying the nucleic acids with at least one PCR primer that anneals to at least a portion of a native HIV-1 proviral sequence encoding Pol.

3. The method of claim 1, wherein the sample of nucleic acids is from a plurality of lymphocytes isolated from the subject.

4. The method of claim 1, wherein the at least one PCR primer that anneals to at least a portion of a native HIV-1 proviral sequence encoding the packing signal sequence comprises a sequence that is complementary to at least about 80% of said portion of said native HIV-1 proviral sequence encoding said packaging sequence.

5. The method of claim 2, wherein the at least one PCR primer that anneals to at least a portion of a native HIV-1 proviral sequence encoding Gag comprises a sequence that is complementary to at least about 80% of said portion of said native HIV-1 proviral sequence encoding Gag.

6. The method of claim 2, wherein the at least one PCR primer that anneals to at least a portion of a native HIV-1 proviral sequence encoding Pol comprises a sequence that is complementary to at least about 80% of said portion of said native HIV-1 proviral sequence encoding Pol.

7. The method of claim 1, wherein at least a portion of a native HIV-1 proviral sequence encoding Env comprises a sequence that is complementary to at least about 80% of said portion of said native HIV-1 proviral sequence encoding Env.

8. The method of claim 3, wherein said subject has previously received at least a portion of an antiretroviral therapy ("ART").

9. The method of claim 3, wherein said plurality of lymphocytes comprise CD4+ T cells.

10. The method of claim 1, wherein said HIV-1 hypermutated proviral Env sequence comprises a guanine to adenine hypermutation.

11. The method of claim 1, wherein said hypermutated HIV-1 proviral Env sequence comprises at least 2 guanine to adenine hypermutations.

12. The method of claim 1, wherein said amplifying comprises a polymerase chain reaction (PCR), a quantitative PCR, a droplet digital PCR, a DNA fluorescence in situ hybridization (FISH), a targeted DNA sequencing, or any combination thereof.

13. The method of claim 1, wherein said sample of nucleic acids comprises genomic DNA.

14. The method of claim 3, further comprising treating said subject.

15. The method of claim 14, wherein said treating comprises administering an antiretroviral therapy (ART), a combination antiretroviral therapy (cART), or a highly active antiretroviral therapy (HAART) to said subject.

16. The method of claim 1, wherein said subject is a human.

17. The method of claim 1, further comprising amplifying the nucleic acids in the presence at least one fourth probe that is specific to a hypermutated proviral HIV-1 packaging signal, and detecting the binding of the fourth probe to a portion of a native HIV-1 proviral packaging sequence.

18. The method of claim 2, further comprising amplifying the nucleic acids with at least one PCR primer that anneals to at least a portion of a native proviral sequence encoding Gag in the presence of at least one fourth probe that is specific to the native HIV-1 Gag proviral sequence.

19. The method of claim 2, further comprising amplifying the nucleic acids with at least one PCR primer that anneals to at least a portion of a native proviral sequence encoding Pol in the presence of at least one fourth probe that is specific to the native HIV-1 Pol proviral sequence.

20. The method of claim 2, further comprising amplifying the nucleic acids with at least one PCR primer that anneals to at least a portion of a native proviral sequence encoding Gag in the presence of at least one fourth probe that is specific to the native HIV-1 Gag proviral sequence and amplifying the nucleic acids with at least one PCR primer that anneals to at least a portion of a native proviral sequence encoding Pol in the presence of at least one fifth probe that is specific to the native HIV-1 Pol proviral sequence.

21. The method of claim 1, wherein detection of the binding of the second probe to the portion of the native HIV-1 proviral Env and the presence of an amplicon generated by amplifying the nucleic acids with the at least one PCR primer that anneals to at least the portion of the native HIV-1 proviral sequence encoding the HIV-1 packaging signal indicates the presence of an intact HIV-1 provirus.

22. The method of claim 1, wherein the absence of the binding of the second probe to the portion of the native HIV-1 proviral Env and the presence of an amplicon generated by amplifying the nucleic acids with the at least one PCR primer that anneals to at least the portion of the native HIV-1 proviral sequence encoding the HIV-1 packaging signal indicates the presence of a 3' defective and/or hypermutated HIV-1 provirus.

23. The method of claim 1, wherein the detection of the binding of the second probe to the portion of the native HIV-1 proviral Env and the absence of an amplicon generated by amplifying the nucleic acids with the at least one PCR primer that anneals to at least the portion of the native HIV-1 proviral sequence encoding the HIV-1 packaging signal indicates the presence of a 5' defective HIV-1 provirus.

24. The method of claim 1, wherein binding of the second probe competes with binding of the first probe in the presence of the native HIV-1 Env proviral sequence.

25. The method of claim 1, wherein the first probe is specific to—the complement of SEQ ID NO: 7, wherein the complement of SEQ ID NO: 7 comprises one or more APOBEC3G hypermutations.

* * * * *